(12) United States Patent
Keating et al.

(10) Patent No.: US 7,803,405 B2
(45) Date of Patent: Sep. 28, 2010

(54) ENCAPSULATION OF AQUEOUS PHASE SYSTEMS WITHIN MICROSCOPIC VOLUMES

(75) Inventors: Christine D. Keating, University Park, PA (US); Marcus R. Helfrich, University Park, PA (US); M. Scott Long, University Park, PA (US); Lauren K. Mangeney-Slavin, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 1338 days.

(21) Appl. No.: 10/439,578

(22) Filed: May 16, 2003

(65) Prior Publication Data
US 2004/0052857 A1 Mar. 18, 2004

Related U.S. Application Data

(60) Provisional application No. 60/411,323, filed on Sep. 16, 2002, provisional application No. 60/283,431, filed on May 17, 2002.

(51) Int. Cl.
*A61K 9/16* (2006.01)
*A61K 9/50* (2006.01)
(52) U.S. Cl. .................................. 424/490; 424/450
(58) Field of Classification Search .......... 424/490
See application file for complete search history.

(56) References Cited

U.S. PATENT DOCUMENTS

| 5,460,831 | A | * | 10/1995 | Kossovsky et al. | 424/493 |
| 5,626,870 | A | * | 5/1997 | Monshipouri et al. | 424/450 |
| 6,143,276 | A | * | 11/2000 | Unger | 424/9.3 |

OTHER PUBLICATIONS

Stenekes et al. The preparation of dextran microspheres in an all-aqueous system: effect of the formulation parameters on particle characteristics. Pharm Res. Apr. 1998;15(4):557-61.*

* cited by examiner

*Primary Examiner*—Jake M. Vu
(74) *Attorney, Agent, or Firm*—McKee, Voorhees & Sease, P.L.C.

(57) ABSTRACT

A means and method for preparing vesicles and freestanding two-dimensional assemblies using aqueous two-phase systems (ATPS) is described. The surface tension of the ATPS is sufficient to support the assembly of various types of particles, and provide the advantage of being biocompatible with DNA and other types of biological molecules that may be used in the assembly. Vesicles are formed by mixing chemically dissimilar compounds in appropriate concentrations and at a temperature sufficient to form a monophasic mixture. This mixture is then heated above the temperature at which the polymer mixture is monophasic, added to a lipid film, and allowed to hydrate at this elevated temperature.

47 Claims, 13 Drawing Sheets

US 7,803,405 B2

SEQUENCE LISTING

```
<160> NUMBER OF SEQ ID NOS: 6

<210> SEQ ID NO 1
<211> LENGTH: 88
<212> TYPE: DNA
<213> ORGANISM: Artificial Sequence
<220> FEATURE:
<223> OTHER INFORMATION: oligonucleotide

<400> SEQUENCE: 1
tacgacttga gaacacagac gtactatcat tgacgcatca gacaacgtgc gtcaaaaatt      60
acgtgcggaa ggagttatcc tgaatgcg                                        88

<210> SEQ ID NO 2
<211> LENGTH: 12
<212> TYPE: DNA
<213> ORGANISM: Artificial Sequence
<220> FEATURE:
<223> OTHER INFORMATION: oligonucleotide

<400> SEQUENCE: 2
cgcattcagg at                                                         12

<210> SEQ ID NO 3
<211> LENGTH: 18
<212> TYPE: DNA
<213> ORGANISM: Artificial Sequence
<220> FEATURE:
<223> OTHER INFORMATION: oligonucleotide

<400> SEQUENCE: 3
aaaaaacgca ttcaggat                                                   18
```

```
<210> SEQ ID NO 4
<211> LENGTH: 12
<212> TYPE: DNA
<213> ORGANISM: Artificial Sequence
<220> FEATURE:
<223> OTHER INFORMATION: oligonucleotide

<400> SEQUENCE: 4
atcctgaatg cg                                                          12

<210> SEQ ID NO 5
<211> LENGTH: 12
<212> TYPE: DNA
<213> ORGANISM: Artificial Sequence
<220> FEATURE:
<223> OTHER INFORMATION: oligonucleotide

<400> SEQUENCE: 5
gcaacggcct ag                                                          12

<210> SEQ ID NO 6
<211> LENGTH: 12
<212> TYPE: DNA
<213> ORGANISM: Artificial Sequence
<220> FEATURE:
<223> OTHER INFORMATION: oligonucleotide

<400> SEQUENCE: 6
tctcaactcg ta                                                          12
```

ENCAPSULATION OF AQUEOUS PHASE SYSTEMS WITHIN MICROSCOPIC VOLUMES

PRIORITY CLAIMS

This application claims priority to U.S. Provisional Applications Ser. No. 60/283,431 filed May 17, 2002 and No. 60/411,323 filed Sep. 16, 2002, the disclosures of which are hereby expressly incorporated by reference.

GRANT REFERENCE

This invention was made with the support from the Government under Grant No. MCB-0074845. The Government has certain rights in the invention.

FIELD OF THE INVENTION

This invention relates to a method of producing aqueous two-phase systems that are suitable for particle manipulation and encapsulation within microscopic volumes.

BACKGROUND OF THE INVENTION

Manufactured products are made from atoms. The properties of those products depend on how those atoms are arranged. For instance, if the atoms in coal are rearranged, they may be used to form a diamond. Viewed from the molecular level, most manufactured articles are very crude and imprecise. Casting, grinding, milling, welding, and all other traditional manufacturing methods spray atoms in large groups. Even lithography is fundamentally statistical and random. Exactly how many dopant atoms are in a single transistor and exactly where each individual dopant atom is located is neither specified nor known.

Nanotechnology offers the ability to work at the atomic, molecular, and supramolecular levels, in a scale of about 1 to 100 nanometers, in order to create, manipulate, and use materials, devices, and systems that have novel properties and functions because of the small scale of their structures. Nanotechnology includes integration of nanoscale structures into larger architectures that may be used in industry, medicine, and environmental protection. Manipulating natural and artificial nano- and micro structures such as cell structures, nanowires, and nanosensors, will be critical to the integration of nanotechnology with device development and manufacturing.

The development of methods for organizing micro- and nanostructures into functional materials with addressable micro-nanoscopic components represents a significant challenge. A variety of methods have been employed to control the assembly of micro- and nanoparticles into ordered one-, two-, and three-dimensional architectures in solution and on surfaces. These invoke three general approaches: 1) the use of organic linker molecules and covalent bonding to generate meso- and macroscopic architectures with control over particle placement within an assembled network of particles; 2) the use of external physical forces (e.g. electric fields) and weak interactions to form ordered 2D particle arrays; and 3) the use of biological molecules and their molecular-recognition properties to guide the assembly of polymeric-network structures either on a surface or in solution.

Biorecognition offers the potential for highly selective nanoparticle positioning. DNA-directed assembly in particular has enormous potential in bottom-up assembly of complex micro- and nanoparticle architectures. A critical challenge in selective nanoparticle assembly lies in controlling the dimensionality of assemblies. Three-dimensional aggregates are readily prepared in solution, and one-dimensional assemblies can be approached by attaching micro- and nanoparticles along the length of a single DNA strand. However, at present there are no efficient methods for assembling such particles in two dimensions. While several groups have demonstrated that particle monolayers or multilayers can be assembled onto solid surfaces via DNA hybridization, to date none of them have successfully prepared freestanding two-dimensional assemblies.

Nanoparticle rafts have been prepared at liquid-air and aqueous-organic interfaces by taking advantage of entropic forces acting on repulsive particles. Unfortunately, however, these interfaces are incompatible with biomolecule stability and bioactivity, including DNA hybridization-driven or protein recognition-driven assembly.

Cells are also filled with nanometer and micron-scale compartments, or organelles, whose location and function can determine the activity of the whole cell. The biological cell can be thought of as a highly functional, complex, self-assembled structure. A typical cell carries out a bewildering number of different biochemical reactions simultaneously, and maintains vastly different chemical compositions in various spatial positions, all within microns of each other.

It would be desirable to design synthetic self-assembled architectures that mimic not only the plasma membrane but also the cytoplasm and internal structures found in biological cells. It would also be advantageous for these synthetic cells to perform typical cell functions, for example: motility, chemotaxis, specialization to form cooperative structures (i.e. tissues, organs, human beings), as well as production of minerals ranging from magnetic particles to hydroxyapatite (bone). Synthetic production of functional cell mimics has tremendous potential in medicine (e.g. drug delivery) and manufacturing (e.g. composite materials with new functions).

Accordingly, it is a primary objective of the present invention to provide a novel method and means of preparing two-phase aqueous interfaces that may be used to assemble particles and design synthetic cells.

It is a further objective of the present invention to provide a novel method and means of preparing two-phase aqueous interfaces for assembling particles using selective recognition chemistry.

It is a further objective of the present invention to provide a novel method and means of preparing two-phase aqueous interfaces for designing synthetic cells that mimic the internal structures and functions of cells.

The method and means of accomplishing each of the above objectives as well as others will become apparent from the detailed description of the invention which follows hereafter.

SUMMARY OF THE INVENTION

The present invention describes a method of forming aqueous-aqueous interfaces using chemically different polymers. The aqueous two-phase systems (ATPS) formed may be used in the assembly of particles and design of model cells. Potential applications of particle assembly at the ATPS interface include particle separations and purification, particle concentration for viewing or chemical derivatization, and biomolecule-directed particle assembly, while synthetic cells may be used to further understand and mimic chemical interactions and reactivity in biological systems. Synthetic cells also may be potentially used in drug delivery systems to treat disease.

The method of the invention involves mixing a few weight percent of two or more chemically dissimilar polymers, such as polyethylene glycol and dextran, in aqueous solution, to form a two-phase interface. The resulting ATPS is characterized by a low interfacial tension of between 0.0001 to 0.1 dyne/cm. This surface tension is sufficient to hold metallic nanowires and other nanoparticles and microparticles. Further, ATPSs are compatible with high ionic strength buffers necessary for DNA-directed nanoparticle assembly, and do not denaturate the biomolecules. It is also possible to prepare multiple phases, such that aqueous polymeric solutions are stacked one atop the next in bulk solutions or as concentric circles or other geometries in microvolumes. This can be accomplished by mixing more than two chemically dissimilar polymers in aqueous solution.

The invention further describes a system and method for preparing giant unilamellar vesicles (GUVs) that encapsulate an ATPS. In forming the vesicles, the chemically dissimilar polymers are mixed in water in appropriate concentrations and under conditions where the solution exists as a single phase. The solution is heated (or cooled) to a temperature at which the polymer mixture is monophasic, added to a dried lipid film, or other type of film suitable for forming the GUV membrane, and allowed to hydrate at this temperature. Following hydration, the vesicles containing ATPS are cooled until phase separation occurs. This method is similar to the preparation of conventional GUVs, except that the aqueous phase in this case is a polymer or polymer/salt solution capable of phase separating after incorporation.

The GUVs of this invention may be used as model cells, designed to mimic not only the plasma membrane, but also the cytoplasm and internal structure found in biological cells. Biomolecules such as proteins and nucleic acids can be partitioned into the various phases within the GUVs to mimic microcompartmentalization that occurs within biological cells, where biomolecules are localized to specific cell regions without being enclosed within a separate membrane within the cell. These synthetic cells have application as test systems for understanding chemical interactions and reactivity in biological systems, and potentially as functional mimics of cell activities (e.g. crawling, chemotaxis).

DETAILED DESCRIPTION OF THE PREFERRED EMBODIMENT

Figure 1:
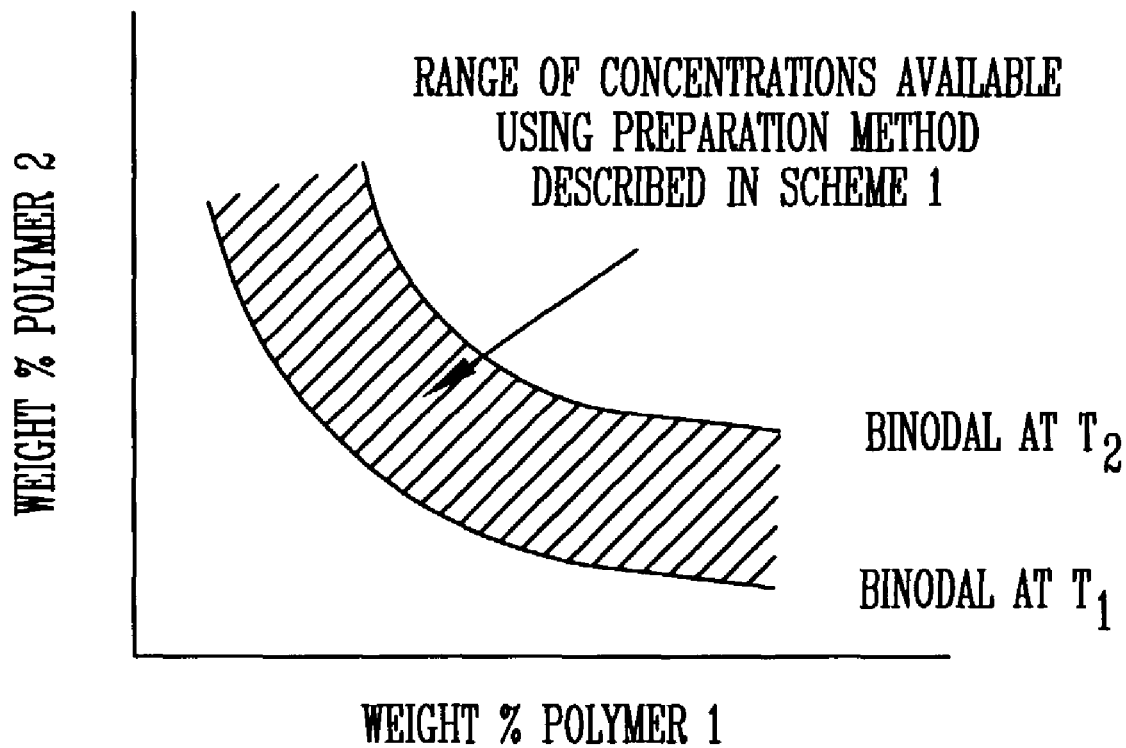
FIG. 1 is a generic representation of a binodal curve for determining the range of concentrations of polymers available for use in preparing the GUVs of the invention.

The present invention relates to the development of aqueous two-phase systems (ATPS) using chemically dissimilar compounds. These ATPS may be used for a variety of purposes, including in the assembly of nano- or microparticles, and in the formation of synthetic cells.

Aqueous two-phase systems have been used in biochemical research for separation and purification of macromolecules, cells, and cell particles. See e.g. P.-A. Albertsson, Partition of cell particles and macromolecules, $3^{rd}$ Edition, Wiley, New York, 1986, the disclosure of which is expressly incorporated herein by reference. In more recent years, ATPSs have also found applications in various areas of biotechnology. However, the present inventors are the first to discover that ATPSs are useful in particle assembly, and in the manufacture of synthetic cells.

As used herein, the term "chemically dissimilar compounds" or chemically incompatible compounds" refer to polymers and/or salts that, when combined at certain temperatures, do not form a uniform solution, but instead form an aqueous two-phase system comprising two immiscible liquids, in accordance with the described invention. Such compounds may also form multiphase systems as mentioned above; these multiphase solutions can also be used for particle assembly or encapsulated within microvolumes similarly to how two-phase systems are employed.

As used herein, the term "vesicle" is defined as vesicles within the conventional sense, as well as porous solids, such as gels, aerogels, sol-gels, or other porous solids, such as porous metals. Further, porous solids encompassing the aqueous systems of this invention may also be encompassed within other vesicles.

The "incompatibility" of certain polymers in aqueous solution was first noted by Beijerinck in 1896. In this case, two phases were formed when agar was mixed with soluble starch or gelatine. Since then, many two-phase aqueous systems have been found, the most thoroughly investigated being the aqueous dextran-polyethylene glycol system (e.g. 10% polyethylene glycol 4000/2% dextran T500), where dextran forms the more hydrophilic, denser, lower phase and polyethylene glycol (PEG) the more hydrophobic, less dense, upper phase. Note that a wide variety of ATPS compositions can be prepared from any given PEG and dextran molecular weight combination. The phase behavior (i.e. the compositions at which phase separation will occur) for any polymer (or polymer-salt) pair is described by a phase diagram; each system has its own experimentally-determined phase diagram.

The formation of two-phase aqueous systems is a phenomenon whereby two different materials that are both soluble in water, but chemically incompatible, result in the formation of two distinct phases, each of which is predominantly water. These systems spontaneously separate into two immiscible liquid phases, each phase being enriched with respect to one of the polymers/salts. The phases have low osmotic pressure and high water content. Salts and other solutes (such as NaCl, $Na_2SO_4$, $HNa_2PO_4$, sucrose, glucose, etc.) can be included to provide the buffering capacity and the tonicity required. The liquid-liquid interface between the phases has a low (and tunable) interfacial tension. These physical properties make polymer two-phase systems very mild for labile materials such as enzymes, cells, and organelles.

As already noted, the two-phase systems are obtained by combining aqueous solutions of two (water-soluble) polymers, differing in their chemical structure, or by addition of a salt (e.g. sulfate or phosphate), at high concentration (typically a few weight percent of each polymer or salt) to a solution of a polymer. For separation purposes in the laboratory, the polymer-polymer type of system has been almost exclusively used, preferentially those consisting of fractionated dextran and PEG.

The theory behind the separation of two polymer phases is complex and not easy to predict. If molecules "prefer" to be surrounded by their own kind instead of being mixed, the energetically favorable state is when the polymers are separated, where one phase contains one polymer and another phase contains the second polymer. The important chemical interactions responsible for determining phase separation are those between segments of both polymers. The interaction between these segments, results from van der Waals interactions, hydrogen bonding, and ionic forces. The driving force in these systems is the large enthalpy of mixing ($\Delta H_m$) associated with the interaction of the long polymer chains. This is opposed by a loss in the entropy of mixing ($\Delta S_m$), which is associated with the segregation of the components into two phases.

$$\Delta G_m = \Delta H_m - T\Delta S_m$$

The above equation shows the relationship between these variables and $\Delta G_m$, which is the Gibbs free energy of mixing. According to the second law of thermodynamics, two components will mix to form a solution when $\Delta G_m$ is negative.

The Flory-Huggins (FH) theory uses a classical, statistical mechanics approach to describe the thermodynamics of phase separation in polymer systems. In general, the FH theory supports the hypothesis that phase segregation occurs from interactions between segments of polymers. The interaction of polymer chains with solvent has little influence on phase separation in FH theory. Flory-Huggins theory explains the different results between mixing polymer segments or mixing monomers. $\Delta S^c$, which is the combinatorial entropy, is associated with the mixture of pure polymer segments with pure solvent molecules. FH theory predicts only positive values of $\Delta S^c$, which indicates that a homogeneous, single phase will form in the absence of intermolecular interactions. It is also predicted that although positive values of $\Delta S^c$ favor mixing and not separation, its contribution to mixing is often significantly less than the entropy associated with small molecules. Therefore, in a system of high concentrations of ethanol and glucose (monomer units of PEG & Dx), the solution is miscible. However, even at low concentrations, these polymers will phase separate. In both systems, the interactions between the components is slightly repulsive, but only in the polymer system does this small repulsive energy overcompensate the energy that favors mixing.

FH theory can also be used to predict phase behavior in polymer-polymer aqueous systems. If, for a given system, $\chi_{ij}$, the Flory interaction parameter, is known, it can be predicted whether separation will occur. $\chi_{ij}$ is dependent on temperature and describes enthalpic interactions between two components.[25] For example, in a system containing water (1) and two polymers (2 and 3), the possible interaction parameters are $\chi_{12}$, $\chi_{13}$, $\chi_{23}$. FH theory predicts that $\chi_{23}$ (interaction between polymers) is always greater than $\chi_{12}+\chi_{13}$ (interaction between each polymer and solvent). The repulsive interactions between unlike polymer segments are stronger than the polymer-solvent interaction.

However, some researchers believe that the solvent, in this case water, does play a role in the separation of polymer phases. Since the solutions of this invention are aqueous, hydrogen bonding occurs between the polymers and water molecules. These interactions compete with polymer-polymer segment interactions. For example, PEG, which is made up of repeating ethylene residues linked by ether bonds, can hydrogen bond two water molecules at each ether oxygen site. This bonding of water alters the geometry of the lattice assumed by water. Dextran can also hydrogen bond water molecules at the hydroxyl groups in the molecules. This theory states that phase separation occurs because two different and incompatible water structures surround the polymers. The chemical structure of the polymers determines if/how water molecules will bond to it and whether the water structure will be altered. Zaslavsky and colleagues have found that this explains why similar effects on a phase system can be produced by essentially different factors (such as temperature or the addition of salts). Zaslavsky, B. Yu, et al., "Structure of water as a key factor of phase separation in aqueous mixtures of two nonionic polymer," *Polymer* 1989, 30, 2104-2111. The only common link between these factors are that all are known to affect the structure of water. This suggests the importance of the structure/state of water in phase separation.

Figure 3:
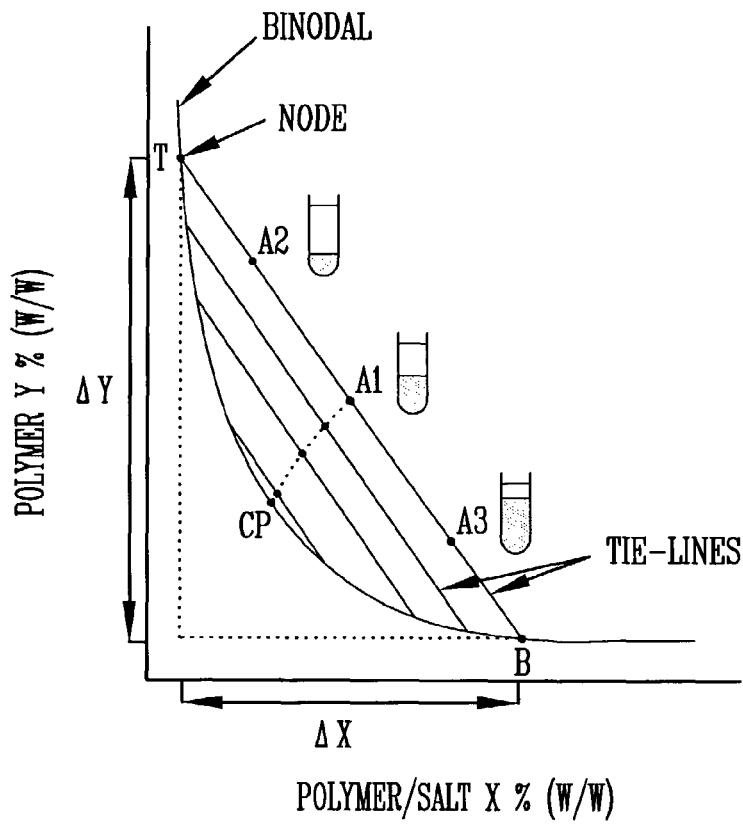
FIG. 3 illustrates a standard phase diagram.

In order to determine at what composition a polymer system will be one or two phases, a phase diagram must be constructed for each system. FIG. 3 shows an example of a standard phase diagram. A phase diagram is a "fingerprint" unique to the system under that particular set of conditions. Phase diagrams are usually plotted with the weight percent of the polymer that partitions to the lower phase on the x axis, and the concentration of the other component on the y axis. For example, in a PEG/dextran system, the high-density dextran forms on the lower phase and the less dense PEG forms on the upper phase. The binodal curve represents the division of concentrations where one or two phases are present. Above this curve, two phases are present, while below it one phase is present. Tie lines give the concentration of each phase when the system is biphasic. Moving along the tie line changes the relative volumes and concentrations of each polymer phase, but the overall concentration in the system remains the same. At the critical point, the compositions of the two phases become the same (volume and concentration). The closer to the critical point of the system, the more sensitive the behavior is to small changes in its environment, such as changes in pH, temperature, and ionic strength.

In general, the position of the binodal curve depends on various factors. Because the compositions obtained from the phase diagram will be used for partitioning and encapsulation experiments, different additives and experimental conditions must be used in order to increase the partitioning between the phases and to make encapsulation possible. The addition of different salts can help with partitioning of different proteins and nucleic acids. The type of salt and the concentration added is also important and can cause changes in the location of the binodal. See e.g. Walter, H. et al., Aqueous two-phase systems, *Methods in Enzymology*, Academic Press Inc.: San Diego, 1994, Vol. 228.

Temperature also has an effect on the binodal position. In general, in PEG/dextrose systems, phase separation occurs at lower polymer concentrations when the temperature is lowered. In some ATPSs, raising the temperature can cause two phases to form. For PEG-containing systems, this occurs from the decrease in PEG solubility at elevated temperatures. For these reasons, a new phase diagram must be constructed for every system with changes in environment. The presence of biological suspensions can also have an effect on the binodal curve and needs to be taken into account when conducting partitioning experiments with biomolecules. Binodals can be determined using methods such as cloud point titration, determination of node points, or turbidometric titration.

Phases form when limiting concentrations of the polymers are exceeded. Both phases contain mainly water and are enriched in one of the polymers. The limiting concentrations depend on the type and molecular weight of the polymers and on the pH, ionic strength, and temperature of the solution. Some polymers form the hydrophobic phase in the presence of fairly concentrated solutions of phosphates or sulfates (e.g. 10% polyethylene glycol 4000/12.5% potassium phosphate buffer). A drawback to the useful dextran/polyethylene glycol system is the high cost of the purified dextran used. This has been alleviated by the use of crude unfractionated dextran preparations, much cheaper hydroxypropyl starch derivatives, and salt-containing biphasic systems.

As noted above, ATPSs are characterized by a low interfacial tension, ranging from about 0.0001 to 0.1 dyne/cm, as compared to 1-20 dyne/cm for organic/aqueous interfaces. The present inventors have found that this tension is sufficient to hold metallic nanowires as large as several μm in length and 300 nm in diameter against gravity, or latex particles several microns in diameter. Importantly, unlike oil/water interfaces, ATPS are compatible with the high ionic strength buffers necessary for DNA-directed nanoparticle assembly. Further, the polymers do not promote the denaturation of biomolecules. In fact, ATPS may be used for cell fractionation and biomolecule purification, as well as nanoparticle partitioning.

ATPSs have been used extensively to separate proteins or other biomolecules in order to remove unwanted impurities from the target species, to separate different conformations or forms of a target protein, or separate solutions containing various proteins or nucleic acids. The localization of target proteins that can occur with large partition coefficients can also be utilized to control where the biomolecule will partition within the bulk ATPS. Extensive research has been performed by Per-Ake Albertsson and others in the investigation of the partitioning of proteins and various factors that affect the extent of separation. The separation of biomolecules between two phases is characterized by the partition coefficient, K.

$$K = C_T/C_B$$

where $C_T$ and $C_B$ are the concentrations of the biomolecule in the top and bottom phases, respectively. The partition coefficient is dependent on various factors. The identity and the concentration of the polymers used is important. As the concentration of the polymers increases and the system moves further away from the binodal, there is a larger difference in the properties between the two phases and the partitioning is more one-sided. K is not generally dependent on the concentration of the biomolecule as long as it is kept below 50 mg/mL.

Although the PEG/dextrose system is quite biocompatible, the chemical differences between the phases are small compared to other two phases systems, such as PEG-salt ATPS. See e.g. Hatti-Kaul, R., "Aqueous two-phase systems," *Mol. Bio.* 2001, 19, 269-277. Small differences in densities sometimes make it difficult to partition certain biomolecules. Besides changing the different factors that affect K (discussed above), additions and alterations can be made to the system to improve partitioning. The use of modified polymers can cause a greater affinity for a charged protein. Both dextran and PEG have been modified with groups that make them either charged or change the hydrophobicity of the group. It is also possible to change the surface properties of the biomolecule in order to make it more likely to partition to one of the ATPS phases. However, when modifying an enzyme it is important to make sure that enzymatic activity has not been lost by the variation. An easy way to improve partitioning without modifying the polymers or the biomolecules is the addition of salt to the ATPS. As discussed before, the addition of salt to an ATPS can alter phase separation and shift the binodal. Even at low concentrations, salt can influence the partitioning of biomolecules. See e.g. Asenjo, J. A. et al., "Model for predicting the partition behavior of proteins in aqueous two-phase systems," *J. Chrom. A* 1994, 668, 47-54.

The mechanism of salt partitioning is not fully understood. As the salt dissolves, it dissociates into ions. These ions have different affinities for the two phases. Pfennig, A., et al., "Consistent view of electrolytes in aqueous two-phase systems," *J. Chrom. B* 1998, 711, 45-52. Johansson has proposed a mechanism for partitioning of salt ions. As discussed before, PEG contains a series of ether groups, which are dipoles and can take part in ion-dipole bonding. Research has supported the presence of anion-PEG complex formation. This would cause the upper, PEG-rich phase to have more of a negative charge than the bottom phase. In general, proteins and single-stranded DNA tend to partition towards the dextran phase at low concentrations of salt. Other possible interactions that affect the partitioning of salt ions include polymer-polymer, polymer-solvent, polymer-ion, and ion-ion interactions.

An electrical potential difference ($\Delta\Psi$) between the phases is created by the nonhomogenous distribution of salt ions. $\Psi$ is dependent on the partition coefficient of the ions. An electrical potential difference is created between the phases if the two ions of the salt have different affinities for the phases. The electrical potential difference affects the partitioning of charged biomolecules. After the salt ions partition, the electrical potential difference creates two distinct ionic environments. When a charged biomolecule is added, it "sees" different ionic compositions and, depending on the charge of the biomolecule, the work necessary for it to partition into the phases is different.

Partitioning in bulk ATPS can be used to control the localization of biomolecules in solution. This system could also be used inside of membrane-bound liposomes to try to control the location of biomolecules inside "cell-like" structures. In creating a synthetic cell model, it would be interesting to compare the partitioning of biomolecules in bulk solution and the confined environment inside liposomes. Liposomes serve as a good small biochemical "container" because they provide the same type of environment as living cells.

Phospholipid vesicles have long been recognized as models for the cell membrane. See e.g. New, R. R. C., *Liposomes: A Practical Approach*; Oxford University Press: New York, 1997. Recently, they have been investigated as reaction vessels and in the development of primitive functional mimics of living cells, in which the biochemical reactions are carried out within the liposome. The cytoplasm of biological cells contains high concentrations of macromolecules (e.g., an *E. coli* cell contains ~340 mg/mL of proteins and nucleic acids). This leads to macromolecular crowding and has been postulated to result in phase separation of the cytoplasm.

Encapsulating systems inside liposomes provides a way to see how decreased volume and increased crowding effects the system. GUVs are composed of a single phospholipid bilayer that encloses a volume. Previous research has been conducted using liposomes as microreactors for biochemical reactions involving enzymes. See e.g. Kaszuba, M. et al., "Hydrogen peroxide production from reactive liposomes encapsulation enzymes," *Biochim. Biophys. Acta.* 1999, 1419, 221-228. Water soluble enzymes can be encapsulated or microinjected within the interior of GUVs and reactions can be monitored in situ and in real time. Walde, P. et al., "Enzymatic reactions in giant vesicles," *Giant Vesicles*, John Wiley and Sons: Chicester, 2000, Vol. 6. Nucleic acids have also been encapsulated within liposomes. Bailey, A., et al., "Efficient encapsulation of DNA plasmids in small neutral liposomes induced by ethanol and calcium," *Biochim. Biophys. Acta.* 2000, 1468, 239-252. It has been proposed that self replication of nucleic acids within lipid membranes was the basis for the origin of life.

The ATPSs of this invention may be formed in the same manner as ATPSs already known in the art, i.e. by combining aqueous solutions of chemically incompatible polymers or a polymer and a salt. While aqueous dextran/PEG systems are preferred, it should be understood that any polymer/polymer or polymer/salt systems that form the requisite aqueous bi- or multi-phasic systems for use in nanoparticle assembly or vesicle formation are also intended to be included within the scope of this invention. Such systems are readily determinable by persons of ordinary skill in the art. Examples of possible polymer combinations include, but are not limited to, cashew-nut tree gum/PEG, PEG/polyacrylamide, starch/PEG, cellulose/dextran, polysaccharides/PEG, agar/starch, dextran/polyethylene glycol polypropylene glycol copolymer, dextran/polyvinylalcohol, dextran/benzoyldextran, dextan/ficoll, hydroxypropyl starch/PEG, polyvinylalcohol/PEG, maltodextran/PEG, pullulan/PEG, poly(vinyl methyl ether)/PEG, dextran sulfate/PEG, carboxymethyldextran/PEG, dextran sulfate/polystyrene sulfonate, potassium phosphate/PEG, ammonium sulfate/PEG, potassium citrate/PEG, magnesium sulfate/PEG, etc. Multiphase systems which include, but are not limited to, any combination of PEG, dextran, Ficoll, dextran sulfonate, and hydroxypropyldextrans can also be used. Such multiphase systems are also well known in the art. The same polymer pair may be used to produce different ATPSs by altering the molecular weight of the polymers. Such different ATPS exhibit different phase behavior.

GUVs made in accordance with this invention exist in a range of sizes as is typically observed for conventional GUVs. Preferred vesicles are generally about 10 μm in diameter and contain two distinct aqueous phases. However, vesicles range in size from submicroscopic to >50 microns in diameter. When these GUVs are prepared, the solution also contains much smaller and some larger vesicles. The smallest vesicles are submicroscopic. In order to utilize liposomes as biochemical reactors and partitioning in bulk ATPS to control where biomolecules partition within ATPS/GUVs, it was necessary to determine conditions for encapsulation. Many aqueous two phase system exhibit temperature-dependent phase behavior, particularly for polymer compositions near the binodal curve on the phase diagram. It should be noted that most commonly used ATPS compositions in the literature are not amenable to encapsulation, as they are far from the bimodal and relatively unresponsive to changes in temperature. Vesicles are prepared above the phase transition temperature of the temperature of the polymer solution. Upon cooling to room temperature, the polymer solution phase separates both within the vesicles and in the bulk solution. These structures are exciting in that they enable the interior volume of liposomes to be structured for the first time. This invention also provides a means for incorporating aqueous phase systems within any microscopic volume, such as lithographically defined features or pores within any number of porous materials or gels (e.g. porous alumina membranes, porous gold, porous silica, etc.).

While many PEG/dextran ATPS compositions near the binodal curve can be converted to a single phase upon heating, some ATPS compositions exhibit the opposite behavior. Indeed, for a given molecular weight of PEG and dextran polymers, compositions which convert to a single phase upon cooling or upon heating can be prepared. This is readily determined from examination of phase diagrams once the position of the bimodal curve at the temperatures of interest is known. This can be determined by cloud point titration, turbidometric titration, or polarimetry. For ATPS compositions that show phase separation upon heating, vesicles can be prepared at a lower temperature (e.g. 4° C. or 25° C.) and then warmed (e.g. 25° C., 37° C., or 50° C.) to induce phase separation.

Temperature is not the only variable which can be changed to induce phase separation after encapsulation of polymeric solutions within microscopic volumes. For instance, a hypertonic solution, such as sucrose, may be used outside the vesicles to increase the osmolarity outside of the liposome. When the osmolarity outside the liposome is greater than that inside the liposome, there is a movement of water from inside the liposome out. This dehydrates the liposome ATPS and cause the polymer concentrations inside the liposome to increase. The addition of sucrose or other hypertonic solution, by increasing the concentration of the polymers inside the liposome, moves the polymer composition away from the binodal. The system is therefore not as dependent on temperature changes. The hypertonic solution is preferably added after the liposomes are formed so as to not to affect the encapsulation process.

Lacking intracellular organelles bound by membranes, the simplest of organisms still display remarkable intracellular organization. For example, the cellular DNA or bacteria is condensed into nucleoids bounded only be cytoplasm. Recently, this has been explained through macromolecular crowding theories. "Macromolecular crowding" refers to the effect(s) of increased thermodynamic activities of macromolecules caused by high concentrations of non-interacting macromolecules, which act as volume excluders.

Excluded volume effects have been investigated in vitro simply by addition of high concentrations of noninteracting macromolecules, such as polyethylene glycol and dextran. For example, DNA ligases which cannot catalyze blunt-end ligation of DNA molecules in dilute solution can do so in high concentrations of noninteracting macromolecules, in accordance with the invention. Volume exclusion has also been shown to affect protein association, the melting behavior of nucleic acids, protein folding, and the polymerization of cytoskeletal proteins. Thus, the reactivities of many well-studied biomolecules may be very different in vivo than as typically studied in vitro.

Phase separation, in which two or more aqueous phases having different macromolecule and salt concentrations arise, can also occur. This type of macromolecule-dependent aqueous separation is believed to occur in living cells, creating microenvironments. The GUVs of the present invention will therefore be helpful in studying and preparing synthetic analogues of the activities of living cells.

The interior of eukaryotic cells is not only crowded by virtue of the large number of dissolved macromolecules, it is also filled with a complex network of insoluble proteins and protein assemblies (i.e. the cytoskeleton), as well as a variety of membranous organelles. In fact, the internal surface area of a single, average-sized cell has been estimated to be on the order of $1\times10^6$ $\mu m^2$. Minton has predicted that equilibrium constants for certain types of reactions may be altered by several orders of magnitude based on confinement within pores of approximately the same size as molecular dimensions. This behavior is expected for processes that involve large changes in the size, shape, or mobility of macromolecules. Living cells use these physical/chemical phenomena (volume exclusion, phase separation) to manipulate the location and reactivity of biomolecules. It is believed these effects can also be used in nonliving systems, such as the GUVs of this invention, to achieve a similar level of control.

To date, investigations of macromolecular crowding have been conducted in macroscopic volumes, and association is determined via centrifugation, light scattering, or a system-specific result (e.g. DNA ligation). The present invention is directed, in part, to microscopic, membrane-bounded volumes. The high surface area to volume ratio in these compartments as compared to a test tube or microcentrifuge tube is significant (a 10 µm vesicle contains but one-half of a picoliter). While several groups have performed biochemical reactions involving macromolecules within liposomes, the relative rates of reaction compared to outside the vesicles have not been reported. In addition, the reaction vessels were much larger than molecular dimensions, where effects of confinement are expected to be unimportant. However, in biological cells, the spaces in which reactants find themselves are often of macromolecular dimensions. Experiments can be conducted inside compartments and in bulk solution to determine the effect of encapsulation.

Compartments comprising, for example, unilamellar liposomes and lithographically-defined depressions in solid substrates can be filled with aqueous solutions containing high concentrations of macromolecules. They can be nanoscale (1-1000 nm) or "cell-sized", ranging from 1-100 microns; animal cells are typically 1-30 mm, while plant cells can be considerably larger, up to 100 nm. Phase separation is observed via optical microscopy, either directly (due to differences in refractive index) or indirectly (via fluorescent tags).

Lithographically-defined depressions in different shapes may be prepared on the GUVs to observe the effect of increased surface area upon phase separation. Fluorescently-tagged dextrans are available in many sizes and may be used to image the phases. By chemically derivatizing the sides and walls of the reaction chambers, it is possible to alter the affinity of the aqueous phases for the surface. This should lead to control over the spatial location of each phase.

Because the interfacial tensions for aqueous-aqueous phase boundaries are so much smaller than those for organic-aqueous or liquid-air interfaces, and because it is possible to fine-tune the interfacial tension simply by altering the concentrations or identity of polymers used in the GUVs of this invention, highly conformal structures result.

Although not as readily derivatized or mass produced as identical test structures, membrane-bounded compartments are more accurate models of biology than the structures already described. Parallel experiments can be conducted in unilamellar liposomes as a function of internal composition and of membrane composition. Five to fifty micron in diameter, "cell-sized" liposomes can be prepared from phospholipids (primarily phosphatidylcholines and phosphatidylglycerols) with up to 0.4 fraction cholesterol via methods described by Akashi and coworkers. *Biophysical Journal*, Vol. 71, 1996 and Vol 74, 1998. The membrane charge and fluidity, as well as the presence of specific headgroup-bound functional groups (e.g. PEG, sugars) can be investigated. Macromolecules (e.g., PEG, dextran, proteins) can be encapsulated within the vesicles during formation, and removed from the external solution by dialysis or centrifugation/resuspension of the vesicles.

An investigation of phase separation in these compartments will generate phase diagrams that can be compared to similar data for the same polymer systems in bulk solution. This will provide information as to whether and how encapsulation within "cell-sized" spaces changes the phase behavior of the macromolecules. The effect will likely be largest for systems in which one of the polymers has appreciable attractive or repulsive interactions with the boundary surface. Phase separation can be identified by refractive index differences between phases, or by a partitioning fluorophore. Understanding how to control phase separation in synthetic cells can lead to better control over the spatial localization of macromolecules and particles.

The present inventors have demonstrated that giant (i.e. "cell sized") unilamellar liposomes (GUVs) are prepared by first forming an ATPS. There are almost an endless number of possible polymer/polymer or polymer/salt combinations that are appropriate for this purpose. The only requirement is that the ATPS composition must be capable of converting to a single phase during encapsulation (e.g. at elevated temperatures), then returning to a two-phase or multiphase system after encapsulation (e.g. upon cooling). In these systems, vesicles often form and collect at the interface. When the external volume is diluted after vesicle preparation but before cooling, vesicles are suspended as in any single-phase system.

The concentrations of the polymer/polymer or polymer/organic salt necessary to form the desired ATPS are identifiable through cloud point titration of the individual polymer or salt aqueous solutions. In short, a solution of one polymer is titrated with the other until the solution becomes cloudy, indicating phase separation. The solution is then diluted with water beyond the point at which it becomes transparent, and the process is repeated. This method gives the location of the binodal curve, which separates the biphasic (above) and monophasic (below) regions of the phase diagram (as shown in FIG. 1). In order to encapsulate the ATPS, liposome hydration must be carried out at a temperature at which the two-phase system is monophasic. Additionally, once the phase diagram is determined, alterations in the composition of the ATPS can be used to control the relative concentrations of the polymers.

The ease of cloud point titrations allows for the rapid generation of two-phase systems that can be readily incorporated into liposomes. FIGS. 2A-2D and 9-13 illustrate a series of separate phase diagrams generated using the cloud point method.

Figure 2A:
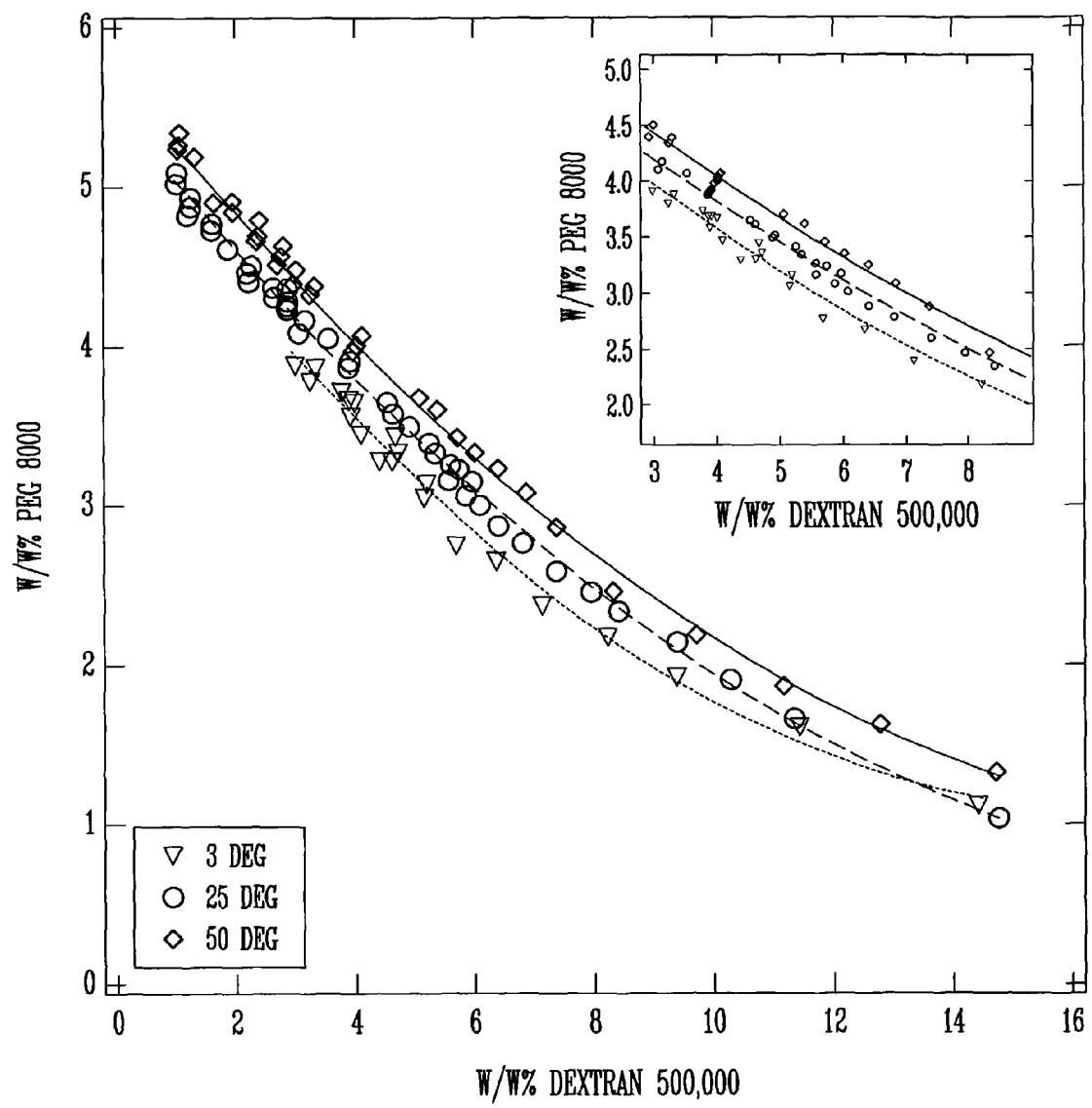
FIG. 2A is a phase diagram of PEG 800/dextran 500,000 ATPS at 3° C. (triangles), 25° C. (circles), and 50° C. (diamonds) using the cloud point method.

FIG. 2A, for example, shows the phase diagram for the PEG 8000/dextran 500,000 ATPS at 3° C., 25° C., and 50° C. as determined using the cloud point determination method. The curves shown are binodals, which delineate the two-phase region (above) from the single-phase region (below). As the temperature is increased, the phase diagram for ATPS-forming polymer/polymer/water mixtures shifts to favor a single phase over two phases. An asterisk marks the composition of the ATPS used in these GUV encapsulation experiments, which lies between the 50° C. and 25° C. binodals. Although the separation between these binodals is quite small, the 3.75° PEG 8,000 g/mol, 4.5% dextran 500,000 g/mol system can be reliably controlled by converting between 50° C. and 25° C. Note that polymer compositions corresponding to any other point between these binodals also meet the temperature conditions necessary for ATPS encapsulation. Choice of different polymer compositions within this range will control the volumes of the two phases. The shift in binodal curve position is as significant between 25° C. and 4° C. as it is between 50° C. and 25° C. Thus, the ATPS formed from this polymer system can be readily converted between one and two phases by adjusting the temperature of the polymer solution from room temperature to 50° C. Phase reversibility is key not only for encapsulation within the vesicles, but also for future applications where the mixing and de-mixing of the phases will be used to control reactions within the enclosed volumes.

Figure 2B:
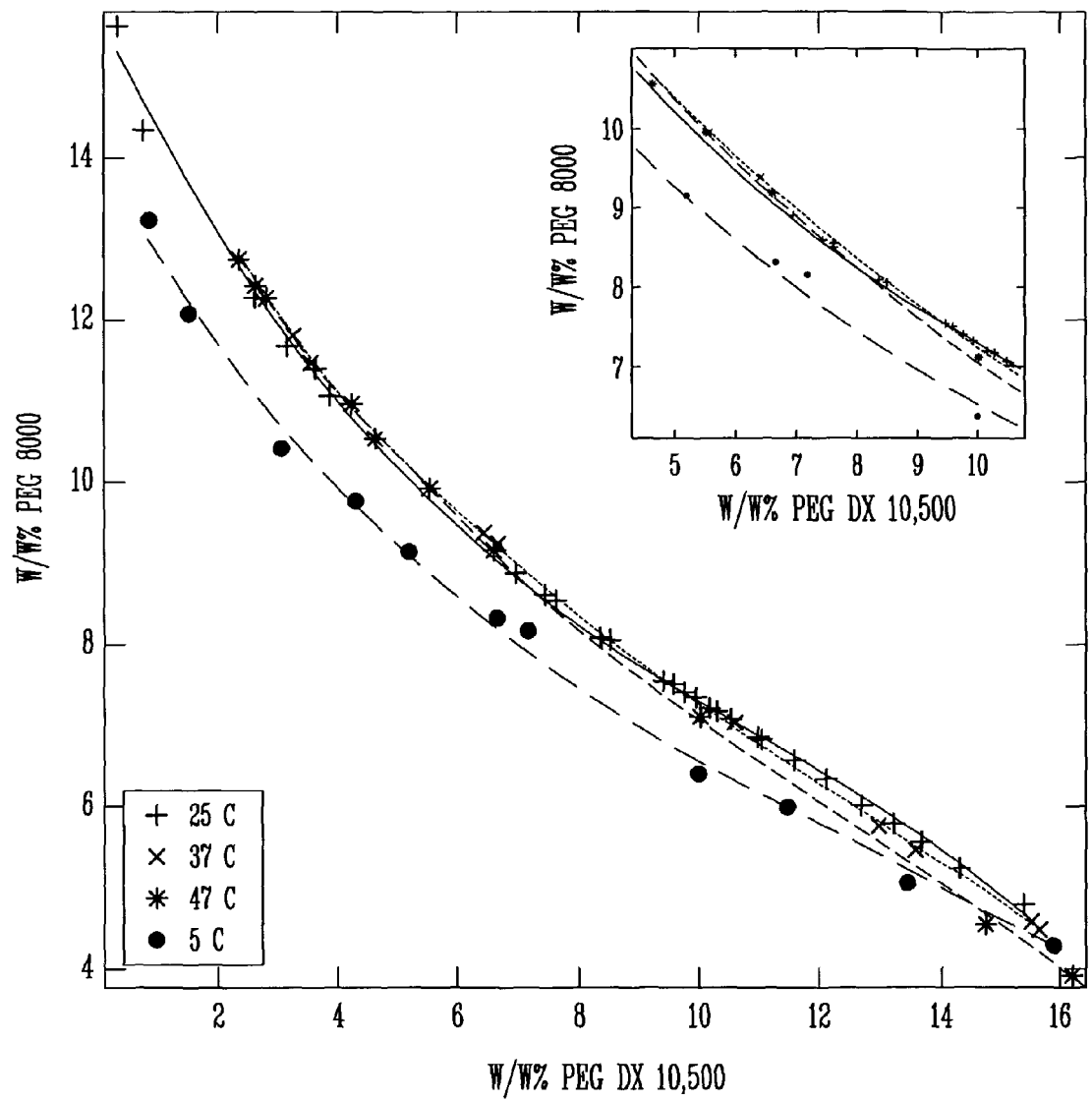
FIG. 2B is a phase diagram of PEG 8000/dextran 10,500 ATPS at 25° C. (plus signs), 37° C. (crosses), 47° C. (asterisks), and 5° C. (solid diamonds) using the cloud point method.
Figure 2C:
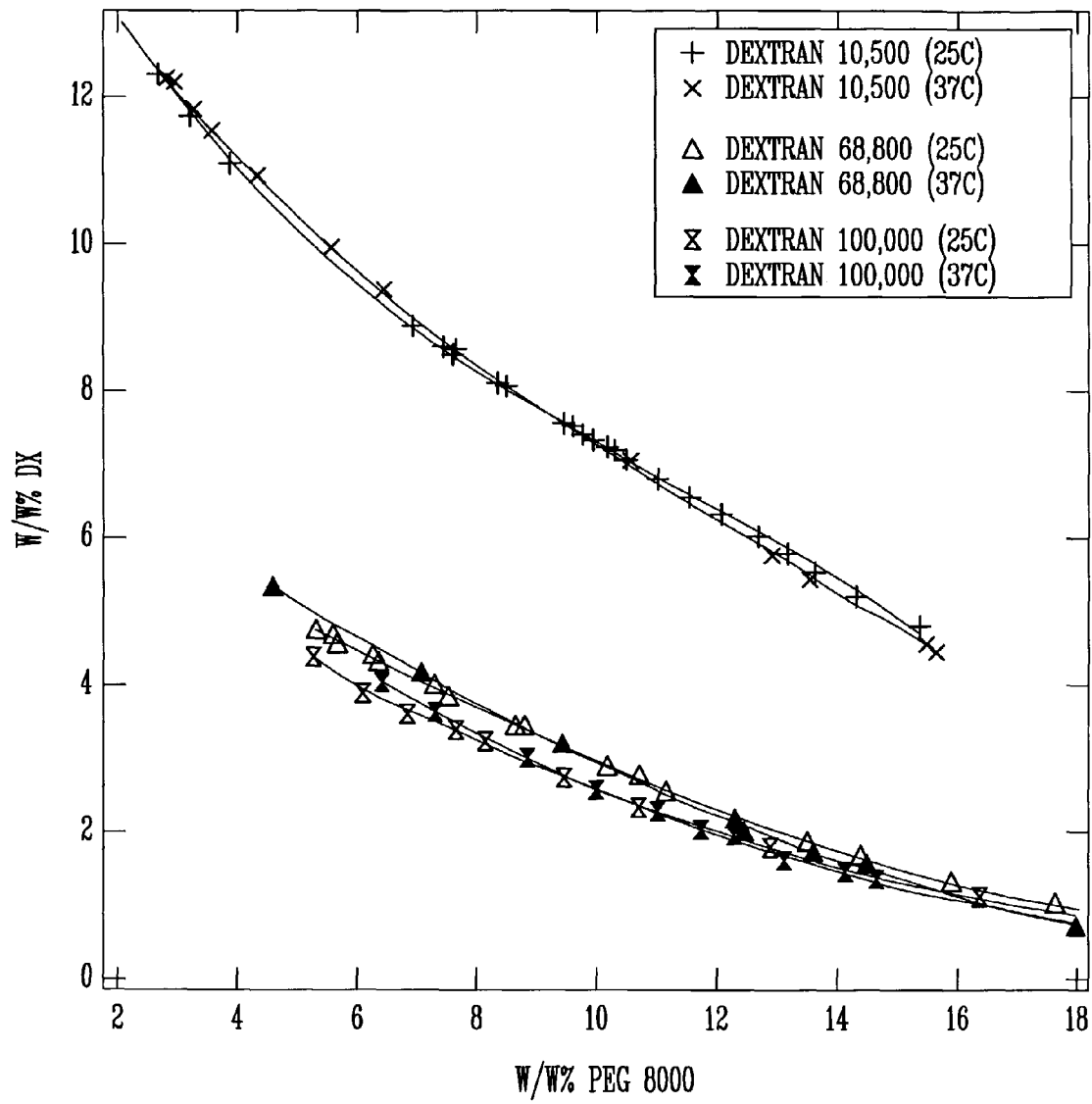
FIG. 2C is a phase diagram of PEG 8000 and dextrans of various molecular weights, each at 25° C. (plus signs, open triangles, and open hour glasses) and 37° C. (crosses, closed triangles, and closed hour glasses) using the cloud point method.
Figure 2D:
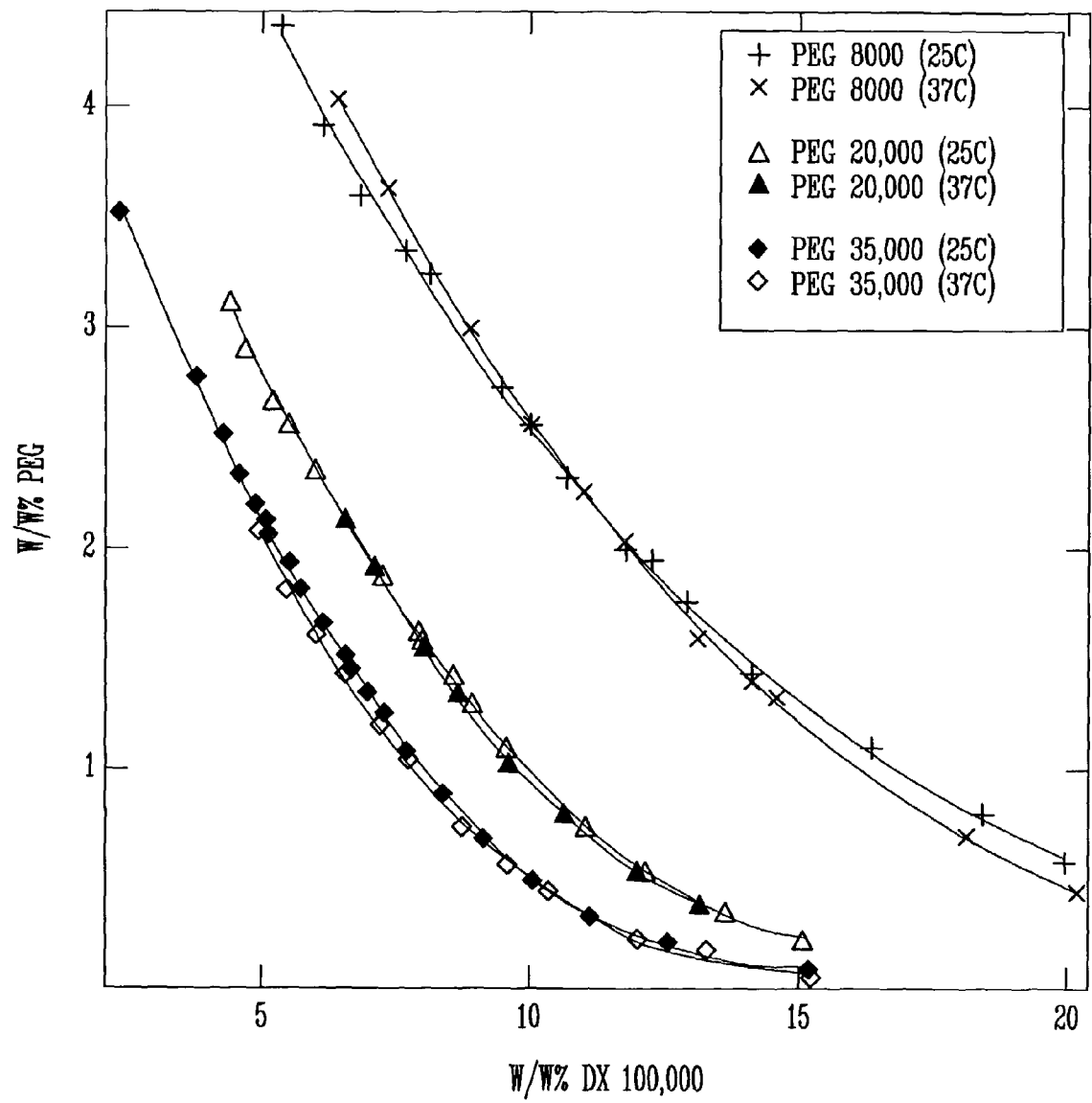
FIG. 2D is a phase diagram of various molecular weight PEGs and dextran 100,000, each at 25° C. (plus signs, open triangles, and closed diamonds) and 37° C. (crosses, closed triangles, and open diamonds) using the cloud point method.

FIGS. 2B-2D show other sample phase diagrams using various polymers. FIG. 2B is a phase diagram of PEG 8000/dextran 10,500 ATPS at 25° C., 37° C., 47° C., and 5° C. using the cloud point method. FIG. 2C is a phase diagram of PEG 8000 and dextrans of various molecular weights, each at 25° C. and 37° C., while FIG. 2D is a phase diagram of various molecular weight PEGs and dextran 100,000, each at 25° C. and 37° C.

FIGS. 9-13 show phase diagrams for different types of PEG and polyacrylamide at various temperatures.

The encapsulation of ATPS within vesicles is not limited to PEG/dextran or PEG/PAA systems, but is applicable to any number of aqueous two-phase or multiple phase systems, all of which are well known to those of ordinary skill in the art. Using the cloud point titration method described above, persons skilled in the art can rapidly generate phase diagrams and encapsulate ATPSs. FIG. 2B is the binodal for the PEG 8000/dextran 10,500 phase system determined using the cloud point titration method. Using this phase diagram, vesicles that encapsulated an ATPS of 8.0 w/w % PEG 8000 and 8.5% w/w % dextran 10,500 were prepared at 37° C. Upon cooling the samples in ice water, phase separation between the polymer was observed within the vesicles.

It is preferred that the ATPS is made fresh immediately prior to its encapsulation for purposes of preventing bacterial contamination, although it is also acceptable to make up the ATPS ahead of time and store according to procedures known in the art. In general, the ATPS is prepared by combining the polymers or polymer/organic salt in water in a clean glass vial, beaker, or other container, until the compounds dissolve. The mixture is then heated (or cooled) to the temperature necessary to convert the ATPS to a one-phase system.

Vesicles are next prepared by placing a thin film of dried lipid, or other suitable membrane-forming compound, in the bottom of a glass vial or other small container. Any type of phospholipid, surfactant, copolymer, or combinations of the same, with or without additives such as cholesterol, membrane proteins, or glycolipids are suitable for this purpose, and may include, but are not limited to, egg phosphatidylcholine, ethanolamine, choline, serine, glycerol, phosphatidylglycerol, myo-inositol, glycerolipids, and sphingolipids. The one-phase ATPS is then added to the vial containing the lipid film, or other suitable film, and allowed to hydrate for a time period sufficient to form vesicles, which is preferably overnight. Following hydration, the vesicles containing ATPS are cooled (or heated) to the temperature at which phase separation occurs, and the liposomes are collected from the interface. These vesicles can be prepared for observation by microscopy. With respect to vesicles prepared using dextran and PEG, the PEG-rich phase is surrounded by the dextran-rich phase, which borders the GUV membrane. In bulk preparations, the more dense dextran-rich phase forms on the bottom of the vesicle.

Using the protocol for vesicle formation described above, lipid-bound functional groups may be incorporated into the liposomal membrane during preparation. To do this, functionalized lipids are mixed with the other vesicle-forming lipids in chloroform, then dried under argon gas to form the lipid film. Other methods known to those versed in the art can also be used. The incorporation of functional groups can be used to direct the location of the phases upon separation (through preferential wetting of the membrane surface), thus providing a way to localize reactions within specific regions of the "synthetic cell". Several such lipids may be incorporated, preferably in concentrations ranging from 1 mole % to 15 mole %, including but not limited to DOPE-PEG 1000, DOPE-PEG 5000, and DOPE-lactose. Using larger more sterically hindered sugars as well as higher concentrations of the lipid-bound functional groups may provide control over the positions of two internal phases. Vesicles may also be doped with up to or greater than 40 mole % of cholesterol or other lipid to reduce the fluidity of the membrane and prevent leakage of the encapsulated polymer phases upon phase separation. Cholesterol is incorporated in the same manner as functionalized lipids, as described above.

Biological macromolecules, such as DNA and proteins, may be partitioned within the vesicles similarly to the partitioning described for bulk ATPS above. As mentioned previously for bulk ATPS, one approach to improve biomolecule partitioning is to add salt to the ATPS mixture that is encapsulated. Vesicles prepared using the procedure described above are stable in salt concentrations up to 10 mM for both KCl and NaCl. Other vesicle preparation protocols have been reported in the literature that enable GUV preparation in up to 2M salt.

In order to characterize the polymer phases following separation, fluorescently-tagged polymers, such as FITC-dextran or FITC-PEG, may be incorporated during preparation of the ATPS prior to encapsulation. Typically, phase separation is visible even in the transmitted light (DIC) images of these vesicles. The ATPS-GUVs appeared as two concentric circles, with different degrees of contrast to the inner and outer shell. The inner circle is the result of the interface that is formed between the encapsulated polymers upon cooling. The identity of the inner and outer phases was determined by imaging FITC-tagged polymers. In every case, the PEG-rich phase was surrounded by the dextran-rich phase, which bordered the GUV membrane. In bulk preparations, the more dense dextran-rich phase forms on the bottom. In microvolumes, the effect of gravity is less important, and surface interactions can dominate. Thus, the phase with higher affinity for the lipid bilayer surface is expected to wet the bilayer preferentially. However, incorporation of 0.05 mole fraction of either PEG 1000 or PEG 5000-modified DOPE lipid within the bilayer during preparation does not reverse the relative positions of the two phases.

ATPSs for use in the manufacture of freestanding 2-D assemblies are made in accordance with ATPSs already known in the art. As noted above, aqueous two phase systems (ATPS) have been used extensively for cell fractionation and for the partitioning of biomolecules and organelles. In 1997, Baxter et al used an ATPS for partitioning of organic and inorganic colloidal particles (*Langmuir* 1997, 13, 3948-3952). However, the present inventors are the first to conduct particle assembly at an aqueous two phase interface.

Advantages of using ATPS for particle assembly are numerous, and include:
the interfacial tension of ATPS can be tuned by selection of polymers, polymer concentration, and buffer or other additional molecules.
very large or very small particles can be confined at the interface
interfacial confinement of particles achieves the following:
 particle concentration
 prevention of particle sedimentation (for heavy particles)
 confinement to two dimensions
In contrast to aqueous-organic interfaces, the ATPS interface is biocompatible. Not only can biomolecules (e.g. proteins, nucleic acids) be partitioned in ATPS, they retain bioactivity and thus can be used in biorecognition-based particle assembly strategies.

Any type of particle may be assembled at the interface of the ATPS, for instance, Au nanowires as small as 3 microns in length and 30 nm in diameter, and as large as 6 microns in length and 320 nm in diameter. Spherical latex particles are also appropriate for assembly. All of these particles become concentrated at the interface of the ATPS upon addition to a preformed ATPS. For particles which normally sediment in solution, addition from the top phase results in particles at the interface, while lighter particles can be added prior to phase separation.

Examples of appropriate particles include, metal (e.g. gold, silver, copper, and platinum), semiconductor (e.g., CdSe, CdS, and CdS or CdSe coated with ZnS), and magnetic (e.g. ferromagnetite) colloidal materials. Other particles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Depending on the composition of the ATPS interface and its resulting surface tension, the size of the particles may range from about 1 nm to about 400 nm (mean diameter), with about 5 nm to about 150 nm being preferred, from about 4 nm to about 50 nm being more preferred, and about 10 nm to about 30 nm being most preferred. The particles may also be rods.

Methods of making metal, semiconductor and magnetic particles are well-known in the art. See, e.g., Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Taransactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky et al., J. Am. Chem. Soc., 112, 9438 (1990); Ushida et al., J. Phys. Chem., 95, 5382 (1992). Suitable nanoparticles are also commercially available from, e.g., Ted Pella, Inc. (gold), Amersham Corporation (gold) and Nanoprobes, Inc. (gold).

Biorecognition may be used to bind particles at the interface surface. Examples of this include DNA hybridization-driven assembly of Au micro- or nanospheres or semiconductor quantum dots onto wires and of wire aggregates at the interface. The ATPS interface also allows for improved assembly of quantum dot assembly onto wires in comparison to assembly in free solution.

For particle assembly using biorecognition, the particles, the oligonucleotides or both are functionalized in order to attach the oligonucleotides to the particles. Such methods are known in the art. For instance, oligonucleotides functionalized with alkanethiols at their 3'-termini or 5'-termini readily attach to gold particles. See Whitesides, Proceedings of the Robert A. Welch Foundation 39th Conference On Chemical Research Nanophase Chemistry, Houston, Tex., pages 109-121 (1995). See also, Mucic et al. Chem. Commun. 555-557 (1996) (describes a method of attaching 3' thiol DNA to flat gold surfaces; this method can be used to attach oligonucleotides to particles). The alkanethiol method can also be used to attach oligonucleotides to other metal, semiconductor and magnetic colloids and to the other particles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67,735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attached oligonucleotides to particles: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

Each particle will have a plurality of oligonucleotides attached to it. As a result, each particle-oligonucleotide conjugate can bind to a plurality of oligonucleotides or nucleic acids having the complementary sequence. Methods of making oligonucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Assembly of oligonucleotides on micro- and nanowires at the interface takes place under conditions effective for hybridization of the oligonucleotides on the particles. These hybridization conditions are well known in the art and can readily be optimized for the particular system employed. See, e.g., Sambrook et al., Molecular Cloning: A Laboratory Manual (2nd ed. 1989). Preferably, stringent hybridization conditions are employed. The rate of hybridization can be increased by heating the interface above the dissociation temperature (Tm) and allowing the solution to cool. The rate of hybridization can also be increased by increasing the salt concentration of the ATPS (e.g., from 0.1 M to 0.3 M NaCl).

The present inventors have surprisingly found that particle-bound biomolecules retain bioactivity at the ATPS interface. Examples of this include enzymatic cleavage of wire-bound dsDNA by a restriction endonuclease, and selective hybridization of complementary oligonucleotides to ssDNA on wires at the interface.

The following examples are provided to further illustrate the invention. They are not intended to limit the invention in any manner.

EXAMPLE 1

Preferred Method of Preparing of APTS Vesicles

For each experiment, the APTS was made fresh immediately prior to its incorporation into the phospholipid vesicles. On average, 6.0 g of the ATPS was prepared for use in an experiment. In a clean vial, 0.225 g PEG 8000 was combined with 0.270 g dextran 500 and mixed until the polymers dissolved. The solids were hydrated with the addition of 5.505 g of water. This mixture was stirred for 30 minutes at room temperature before being heated to 50° C. Once at this temperature, the solution was cooled to room temperature and the layers were first allowed to separate. The solution was again heated to 50° C. and thoroughly mixed before incorporation into the vesicles.

To incorporate into the vesicles, 990 µl of the above ATPS was added to a small flask along with 10 µL of 0.1% w/w FITC-Dextran 500 (in 0.1% w/w dextran 500). This solution was heated to 50° C. and mixed before being pipetted into the flask containing the dried lipid film. Giant unilamellar vesicles were prepared from a dried lipid film using modifications of the procedure of Akashi and co-workers described in the *Biophysical Journal*. In short, the lipid film was prepared by drying a mixture of 90 µL egg PC (10 mg/ml) with 10 µL of DOPG (10 mg/ml) in CHCl$_3$ along with 2 µL of PE-Rhod (0.33 mg/ml) under argon. The lipids were dehydrated under vacuum for 6 hours before hydration overnight at 50° C. with the fluorescently labeled ATPS. Following hydration, the lipid solutions were cooled to room temperature and the pink (due to rhodamine-tagged lipid) liposomal layer collected via pipet. This layer was used to prepare samples for observation by microscopy.

EXAMPLE 2

Method for Improving Partitioning after GUVs are Prepared

Encapsulation-Addition of Sucrose

The goal of the partitioning experiments was to determine conditions for biomolecules to have maximum partitioning into one phase in order to encapsulate the system within a liposome and control the localization of the molecule. Due to the fact that it is necessary to choose a polymer system close to the binodal in order for phase separation to occur at reasonable temperatures, partition coefficients were not as one-sided as hoped, even in the presence of salt. If K=1 for a certain biomolecule, when partitioned, it is expected that both phases inside the liposome would fluoresce equally. In the inventors' lipid system, the concentration of salt is also a limitation to encapsulation. In some cases, with this particular liposome preparation, liposomes will not form in the presence of 50 mM (or above) salt. Because of this, another method was used in order to improve partitioning and separation without preventing the encapsulation of a one-phase ATPS. The addition of 0.5M sucrose was used both to dilute the bulk fluorescence for the microscope samples and to cause a change in the osmolarity of the liposomes. When the osmolarity of the inside and outside volumes of the liposome are equal, the concentration of the polymer system within the liposome remains the same. However, when the osmolarity outside the liposome is greater than that inside the liposome, there is a movement of water from inside the liposome out. This dehydrates the liposome ATPS and cause the polymer concentrations inside the liposome to increase. This effect can be utilized to improve partitioning. In addition, at the time that these experiments were conducted, it was not possible to cool the stage of the microscope to 3° C., which would be needed to view two phases inside the liposomes. The addition of sucrose, by increasing the concentration of the polymers inside the liposome, moves the polymer composition away from the binodal. Therefore, the system is not as dependent on temperature changes. The sucrose was added after liposomes were formed, so it did not affect the encapsulation process.

Encapsulation at Room Temperature

In addition to ATPS encapsulation at 50° C., encapsulation has been conducted at a lower (25° C.), more "enzyme-friendly" temperature in order to avoid loss of enzymatic activity. The main difference between the liposome preparation at different temperatures was the time permitted for encapsulation. At room temperature, a longer encapsulation time (40 hours) is needed, compared to encapsulation at 50° C. (20 hours). Initially, FITC-PEG and FITC-Dx were partitioned in the liposomes. Photographs of the ATPS/GUVs under an optical microscope show that the FITC-dextrose partitions to the outer phase. From bulk partitioning results, the dextran must be the outer phase and the PEG must be the inner phase. This is supported by the encapsulation of FITC-PEG. The FITC-PEG partitions into the inner phase. The partitioning of FITC-PEG shows the effect of the addition of sucrose. For FITC-dextrose, the partitioning in bulk is very one-sided towards the dextran phase, so visible separation is expected inside the liposome, even without the addition of sucrose. The partition coefficient of FITC-PEG in solution is only 1.47. However, within liposomes, the partitioning is clearly visible.

A line scan analysis was performed to estimate the partition coefficient of the fluorescently-labeled polymers inside the liposomes. The average partition coefficient for FITC-Dx was calculated to be K=0.85+/−0.05 inside the vesicle. The average K for FITC-PEG was 1.66+/−0.41. These values do contain some error because it is a far field microscope image. Fluorophore that is out of the plane of focus still shows up, causing the results not to be completely accurate.

Experimental Details for 2 and 3

Materials:

All reagents are commercially available and used without further purification, except for a DNA strand consisting of 88 nucleotides, which was synthesized in-house. All water used was from an 18 MΩ Barnstead Nanopure water filtration/purification system. Poly(ethylene glycol) (molecular weight 8000-Lot #71K0150) and dextran (molecular weight 482000-Lot#81K1082 and molecular weight 505000-Lot#32K1454), catalase (from bovine liver), and horseradish peroxidase-fluorescein isothiocyanate (FITC-HRP) were from Sigma. (Note: lot numbers are reported for the polymers due to molecular weight differences between different lots). An Alexa Fluor™ 488 protein labeling kit was purchased from Molecular Probes and used to fluorescently label the catalase. Sodium phosphate and chloroform were purchased from EM Science. Sodium chloride was obtained from VWR. Albumin from bovine serum-fluorescein conjugate was purchased from Molecular Probes. Fluorescein isothiocyanate-dextran (molecular weight 500000) (FITC-Dx) conjugate was from Fluka. Fluorescein-PEG-NHS (molecular weight 5000) (FITC-PEG) was purchased from Shearwater Polymers, Inc. L-α-Phosphatidylcholine from egg (egg PC), 1,2-dioleoyl-sn-glycero-3-[phospho-RAC-(1-glycerol)] (DOPG), and phophatidylethanolamine (lissamine rhodamine B) (PE-Rhodamine) were purchased from Avanti Polar Lipids, Inc. Sucrose was obtained from Fisher Scientific.

The 88-base DNA oligonucleotide synthesized in house had a sequence of TAC GAC TTG AGA ACA CAG ACG TAC TAT CAT TGA CGC ATC AGA CAA CGT GCG TCA AAA ATT ACG TGC GGA AGG AGT TAT CCT GAA TGC G (SEQ ID NO:1) with a 5' 6-FAM group attached. The 12-base DNA oligonucleotide, purchased from Integrated DNA Technologies, had a sequence of CGC ATT CAG GAT (SEQ ID NO:2) with a 3' 6-FAM group attached.

Instrumentation:

Optical Microscope: A Nikon TE300 Eclipse inverted optical microscope with a Xenon arc lamp from Sutter Instrument Company was used to view liposome samples. A Plan Fluor 100× oil immersion lens (N.A.=1.3) was used. Differential interference contrast (DIC) was necessary in order to see the liposomes. Samples were mounted on a glass slide using a Secure-Seal spacer (Molecular Probes Inc.) and a glass cover slip. Once prepared, samples were kept in the refrigerator (~3° C.), in the dark, for about our hour before viewing. The microscope stage was equipped with a connection to a water bath, in order to control the temperature. Image Pro Plus software was used to manipulate and save images. Fluorescence images were acquired using Nikon filter cubes. In order to view the FITC-polymers, FITC-proteins, or 6-FAM DNA oligonucleotides, a cube was used with an excitation of 465-495 nm and an emission of 515-555 nm. To see the Rhodamine B dye in the lipid bilayer, a "wide green" cube was used, with an excitation of 515-555 nm and an emission of >590 nm.

Fluorescence Spectroscopy: Fluorescence was used in the partitioning experiments to determine the intensity of the fluorescent biomolecule in each phase of the ATPS. Calibration curves were made in order to determine concentrations. Fluorescence was measured using a Jobin Yvon Horiba Fluorolog-3 model with Datamax software.

Refractometer: The refractometer was used to measure the refractive index of the polymer stock solutions before performing cloud point titrations. A calibration curve was constructed for both PEG and dextran so that the concentration of the solutions could be calculated. The refractomer used was from Leica Auto Abbe, model # 10500B.

DNA synthesizer: An Applied Biosystems Expedite (#8909) DNA synthesizer was used to make the 88mer DNA oligonucleotide strand.

Confocal microscopy: An Olympus Fluoview 300 Confocal Laser Scanning Microscope was used from the Center for Quantitative Cell Analysis. A line scan of 88-base DNA partitioning within liposomes was analyzed using Fluoview software and Microsoft Excel.

Construction of Phase Diagrams:

All phase diagrams presented here were constructed using PEG 8000 and dextran (dextran was either molecular weight 482000 or 505000 Da). Phase diagrams were made following either the cloud point titration method or the turbidometric titration method.

Figure 4:
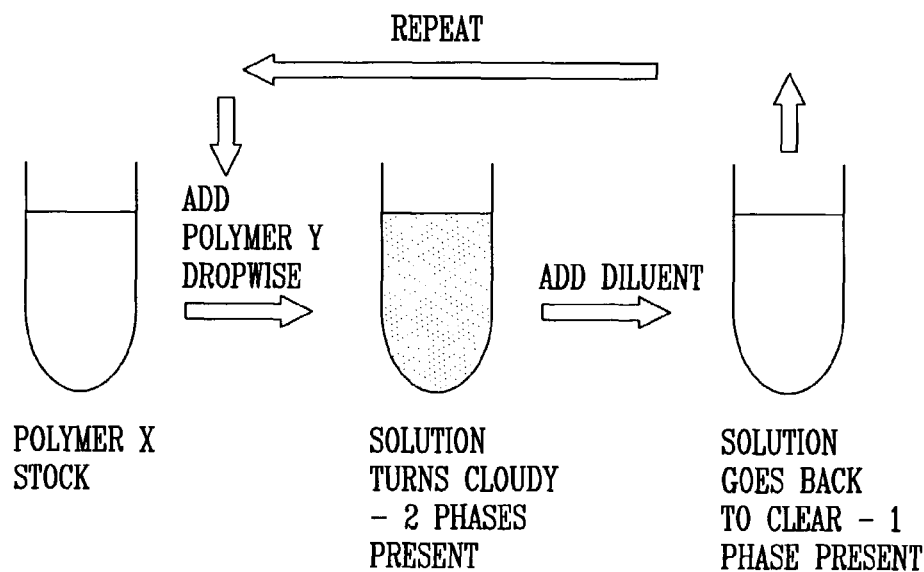
FIG. 4 is a schematic of the protocol for the cloud point titration method.
Figure 5:
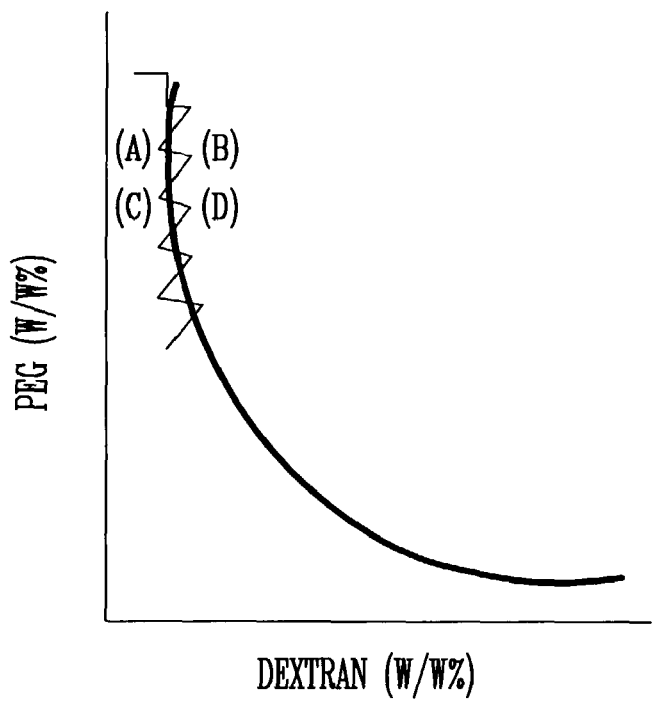
FIG. 5 is a sample phase diagram for the cloud point titration method. Starting at (a), the system consists of PEG and is one phase. Dextran is added until the solution turns just cloudy (b) and two phases form. Water or buffer is then added to dilute the polymers to revert to one phase (c). The addition of dextran is then repeated to cloudiness (d).

A schematic of the protocol for the cloud point titration method is shown in FIG. 4. In short, concentrated polymer stock solutions were prepared. A vial is weighed with an addition of about 3 grams of the dextran stock solution. The stock solution of PEG is added drop wise, with magnetic stirring, until the first sign of turbidity. This signifies that two phases have now been formed and this point is located on the binodal. The vial is then weighed and the mass of the added PEG can be calculated. A known amount of diluent (either water or buffer) is then added to return the solution to clear and the titration is repeated. From the mass of the PEG added, the concentration of each polymer at the transition point (from clear to cloudy) can be calculated and represents a point on the binodal. FIG. 5 shows a sample phase diagram and how this method determines the points that lay on the binodal. Titrating the samples continuously crosses the binodal at different points along the curve.

Figure 6:
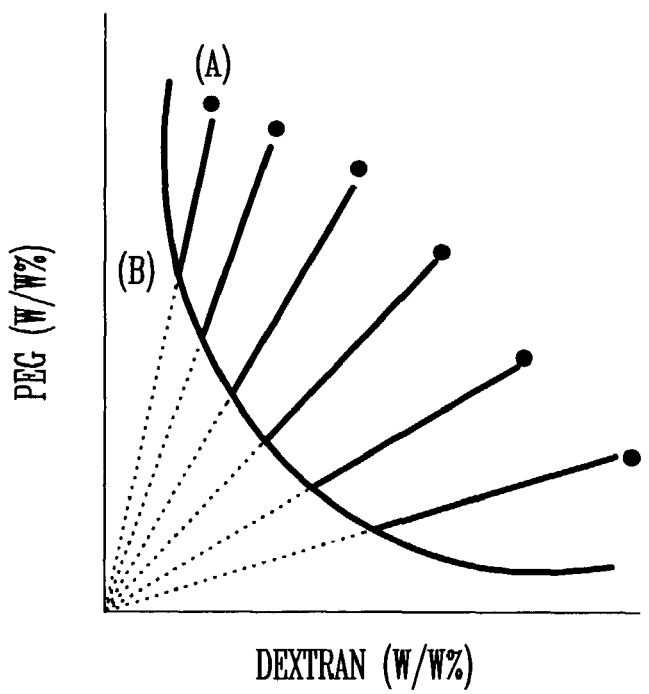
FIG. 6 is a sample phase diagram for turbidometric titration method. Polymer compositions are prepared that form two phases (a). Water or buffer is added dropwise until system just turns clear. This dilutes the polymers until one phase is formed. This point lies on the binodal (b). Multiple samples are made and diluted in this manner.

The protocol for the turbidometric titration method involves making up individual systems, containing both polymers, at concentrations where the system separates into two phases. Because there are two phases present, the solution initially appears cloudy. Either water or buffer is added drop wise, while mixing with a magnetic stirbar, until the solution just turns transparent. This signifies crossing over the binodal, going from two phases to one. A sample phase diagram constructed using this method is shown in FIG. 6. In this method, multiple systems were made up in order to get the most points on the binodal, and thus a more accurate curve.

Phase diagrams were performed at different temperatures (3° C., 25° C., 50° C.) and in different sodium chloride (1, 2, 3 mol/kg NaCl) concentrations to investigate the effect of ionic strength on the position of the binodal. Original phase diagrams were constructed using water as the diluent. For the cloud point titration method, when salt is introduced into the system, the concentrated polymer solutions are prepared with the correct concentration of salt added. The diluent used is a buffer solution containing the same concentration of salt, so that as titrations were repeated, the concentration of the salt remained the same. For the turbidometric titration method, the original system was made in the presence of salt and the diluent is again a buffer solution containing the same concentration of salt.

The points on the binodal, as determined from the above methods, were plotted as concentration of PEG versus the concentration of dextran. Lines were plotted based on a polynomial best-fit line to the data in order to help guide the eye.

Synthesis of Aqueous Two-Phase Systems

To prepare an ATPS, dry polymers were added together in the "correct" ratio (as determined from the phase diagram). If the system is to contain salt, the dry salt was also added to the polymers before being diluted. These components were then diluted with either distilled water or buffer. ATPSs were stirred magnetically until all polymers were dissolved. ATPS compositions were tested by heating the samples to the elevated temperature, then cooled to the lower temperature. The system should go from one to two phases at these temperature transitions. These ATPS compositions were used in partitioning and encapsulation experiments.

Figure 7:
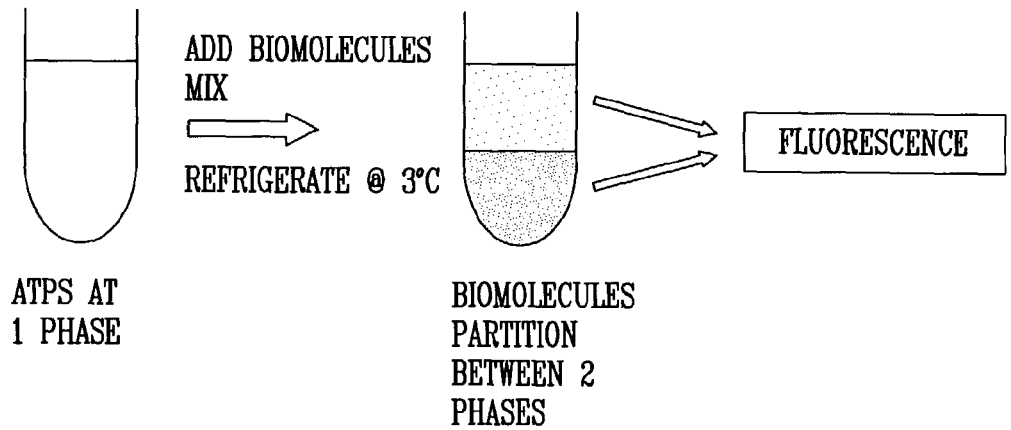
FIG. 7 illustrates a scheme of biomolecule partitioning experiments.

Partitioning of Biomolecules or Fluorescently Labeled Polymers:

FIG. 7 shows a scheme of how partitioning experiments were performed. 990 μl of ATPS were prepared as above and 10 μL of fluorescently labeled biomolecule were added when the ATPS was at one phase (room temperature). The different biomolecules partitioned included: two DNA oligonucleotide strands (an 88-base and 12-base oligonucleotides), BSA, catalase, and HRP. FITC-dextrose and FITC-PEG were also partitioned. Solutions were mixed and refrigerated at 3° C. until two phases separated out. Top and bottom phases were analyzed via fluorescence. The partition coefficient was then calculated.

Figure 8:
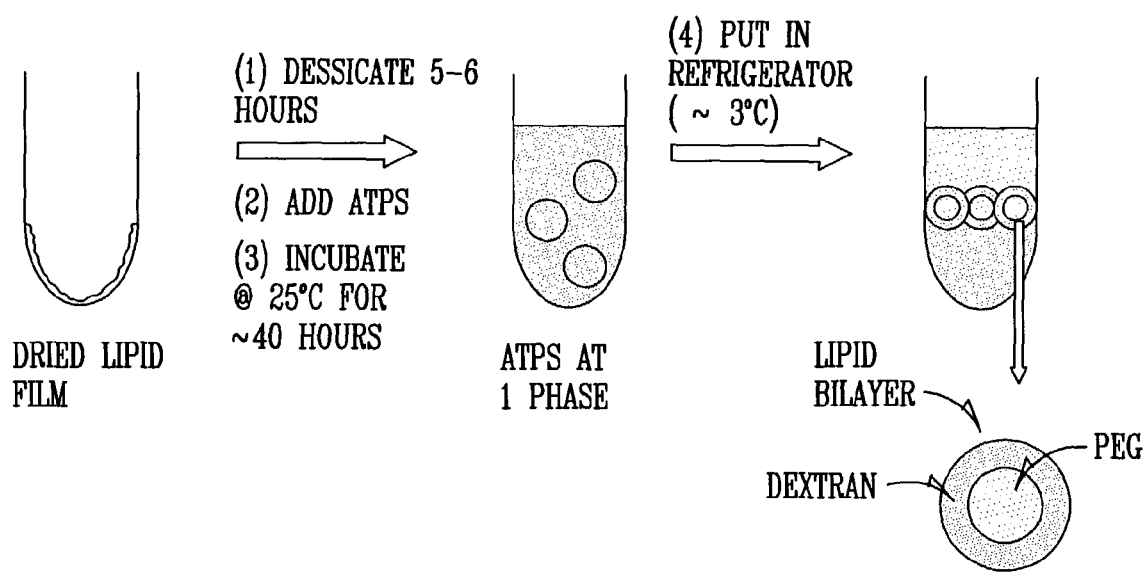
FIG. 8 illustrates a scheme of liposomal preparation and encapsulation of ATPS.
Figure 9:
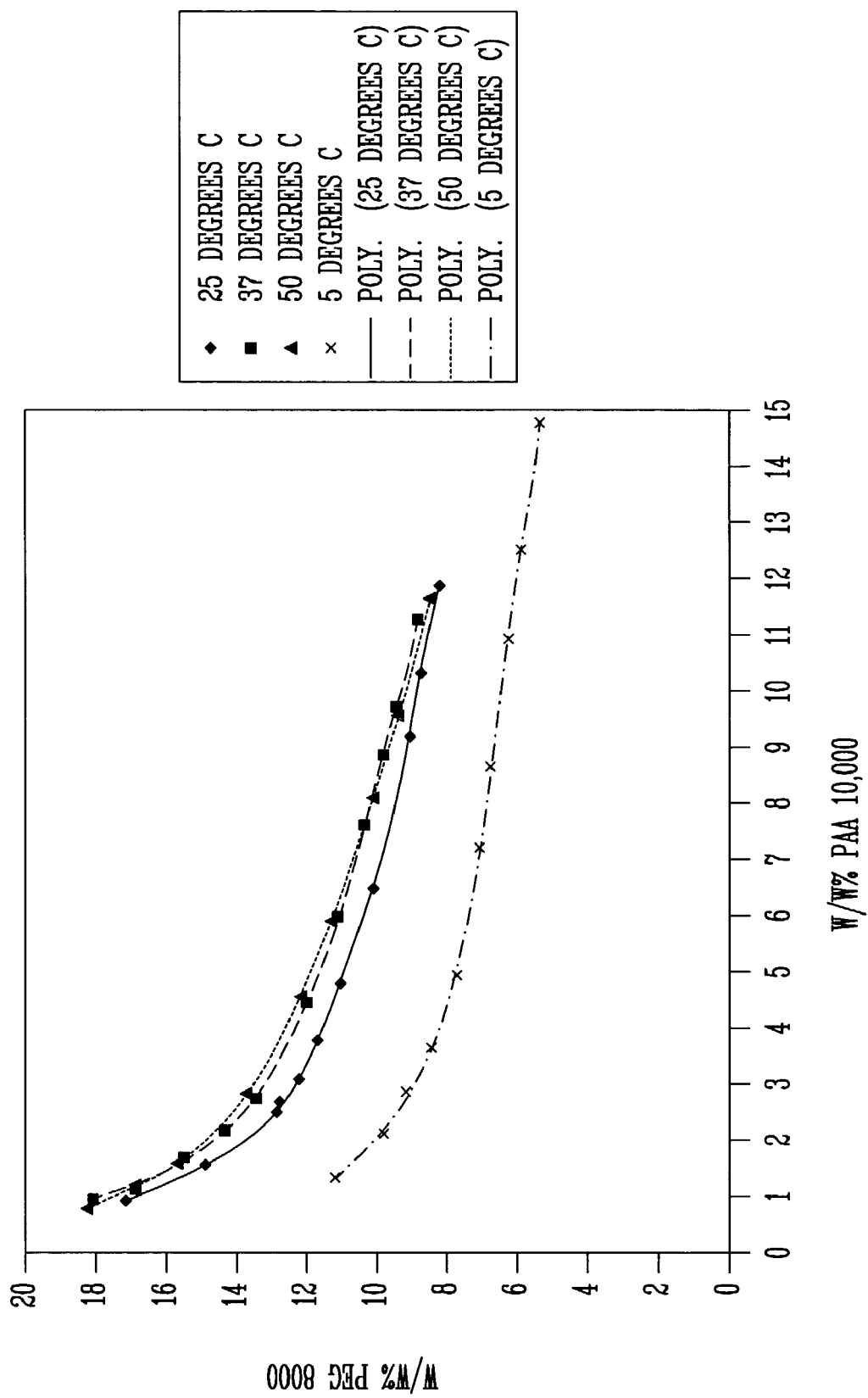
FIG. 9 is a phase diagram of PEG 8,000 and polyacrylamide (PAA) 10,000 at 25° C., 37° C., 50° C., and 5° C.
Figure 10:
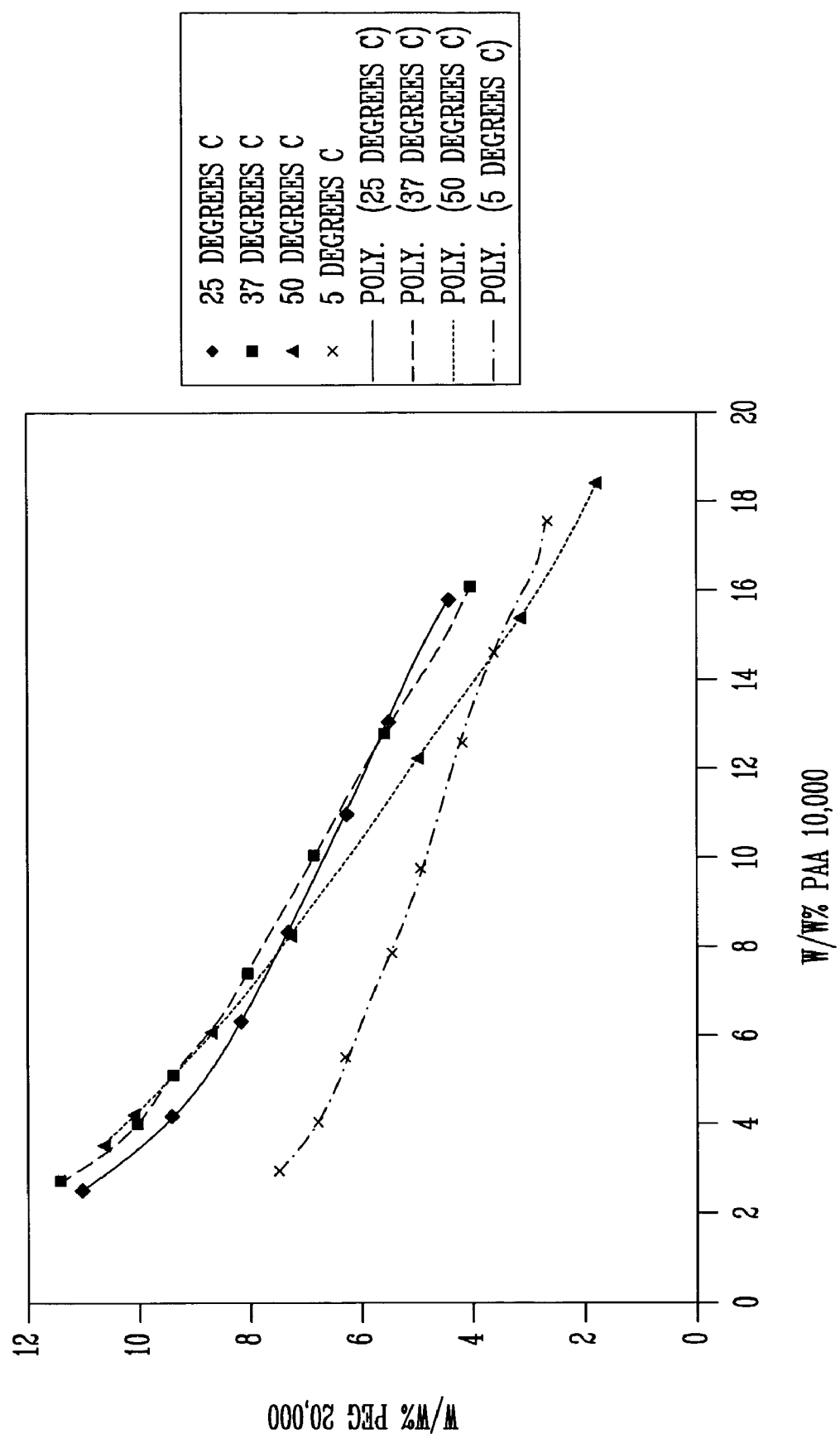
FIG. 10 is a phase diagram of PEG 20,000 and polyacrylamide (PAA) 10,000 at 25° C., 37° C., 50° C., and 5° C.
Figure 11:
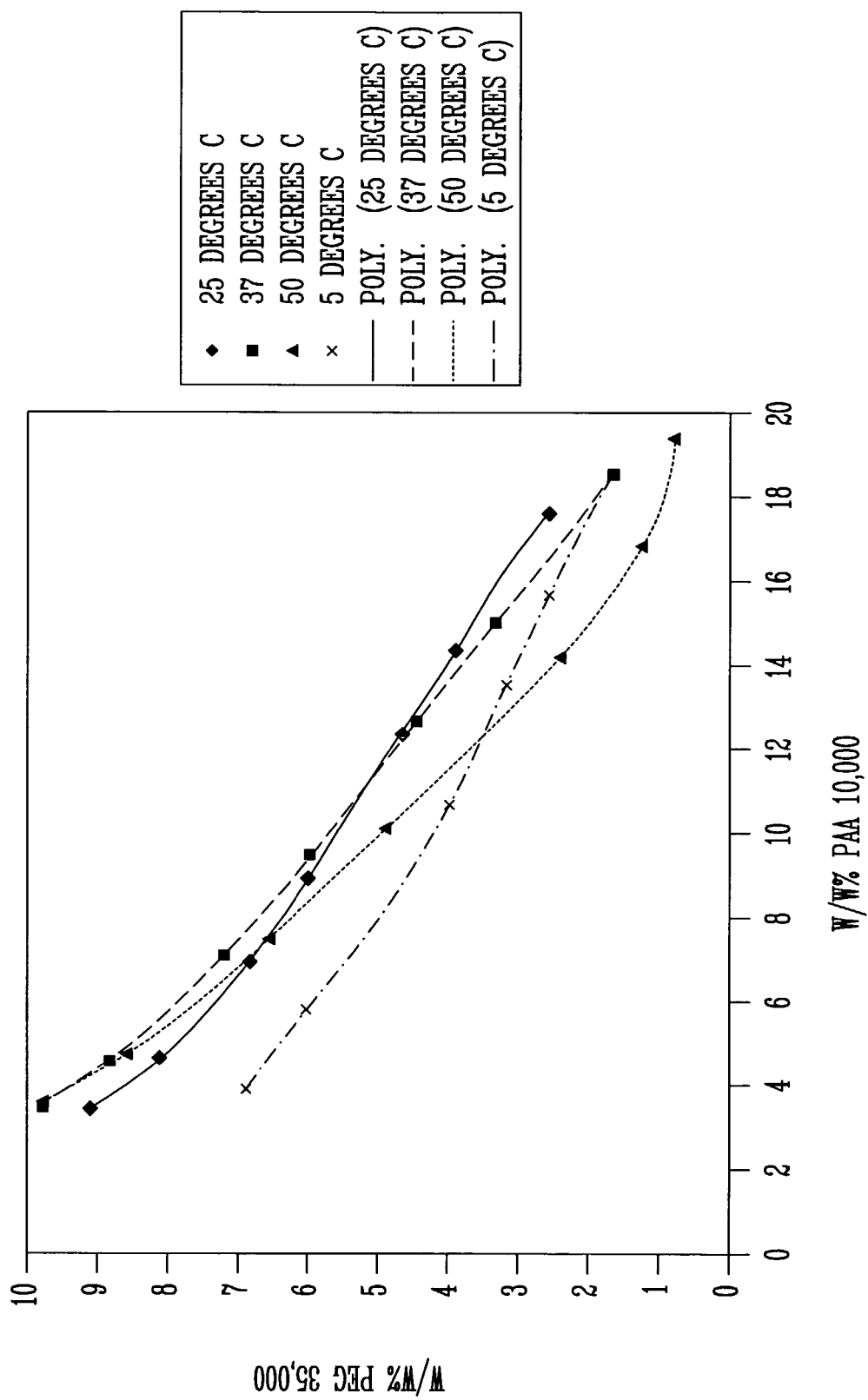
FIG. 11 is a phase diagram of PEG 35,000 and polyacrylamide (PAA) 10,000 at 25° C., 37° C., 50° C., and 5° C.
Figure 12:
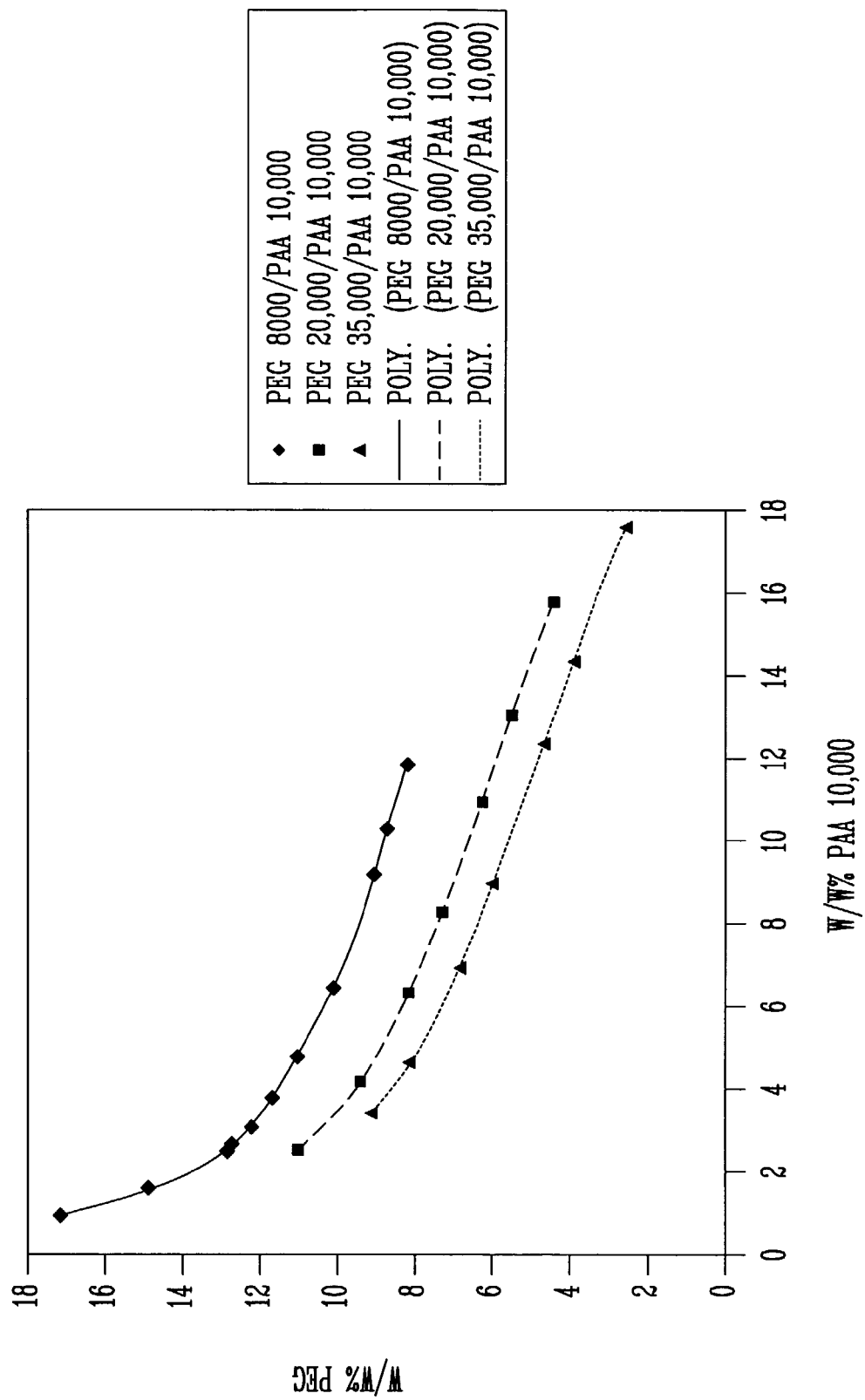
FIG. 12 is a phase diagram of various weight PEG (8000, 20,000 and 35,000) and polyacrylamide (PAA) 10,000.
Figure 13:
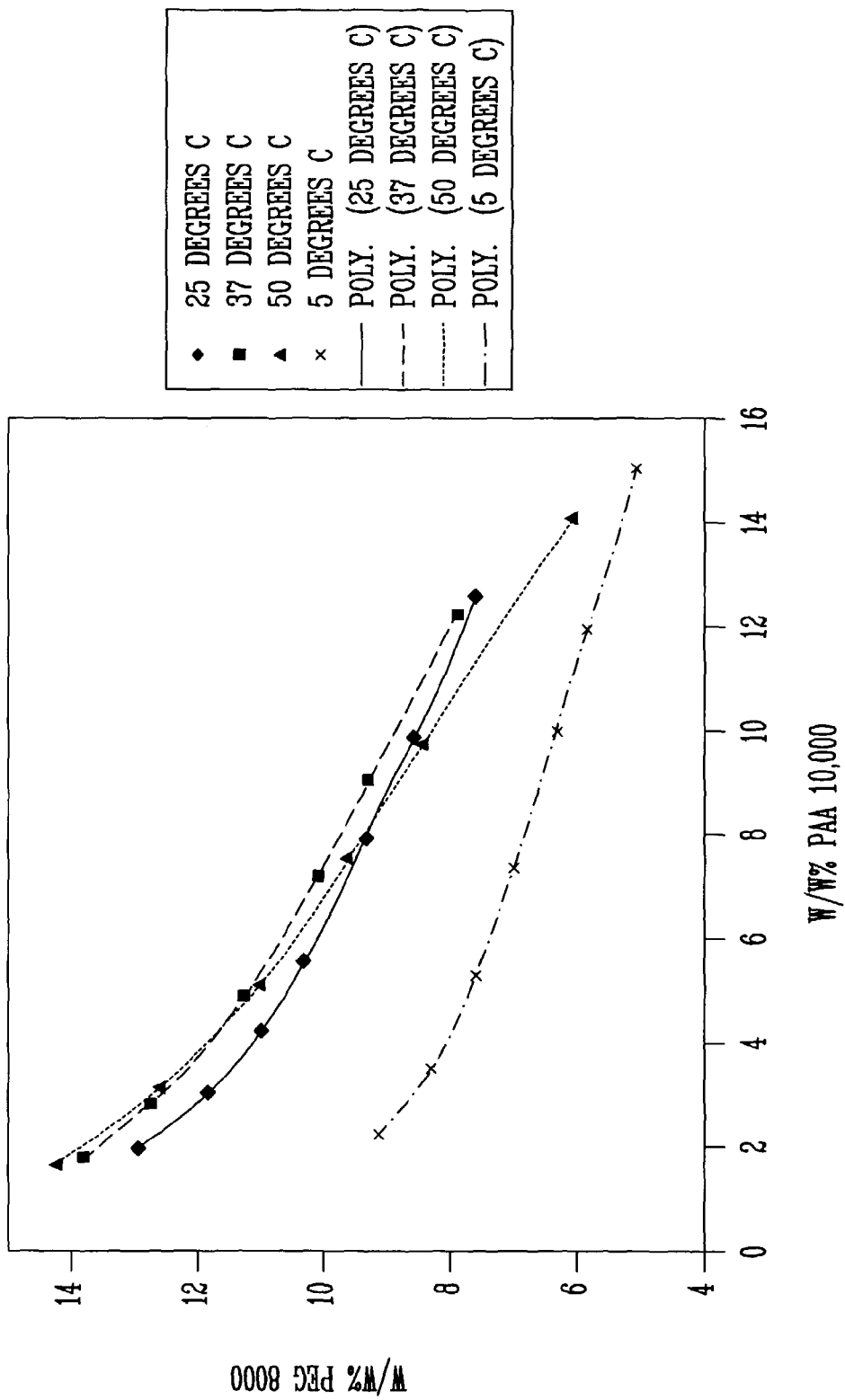
FIG. 13 is a phase diagram of PEG 8,000 and polyacrylamide (PAA) 10,000 at 25° C., 37° C., 50° C., and 5° C. in 64 mM pH 7 phosphate buffer.

Preparation of ATPS Encapsulated Liposomes:

FIG. 8 shows a scheme of the liposome preparation method. Liposome preparation was modified from published protocols. Liposomes were composed of two different parts: the main phospholipids, which were in the highest concentration, and a fluorescently-tagged lipid. All liposomes presented here were in a 9:1 ratio of egg PC to DOPG. PE-Rhodamine was also used in all experiments at <0.05 mol percent. All lipid solutions were stored in argon at −20° C. The lipid samples were mixed until homogeneous and then dried with argon to evaporate the solvent and desiccated under vacuum for 5-6 hours to form a lipid film. Lipid films were then prehydrated with water-saturated Ar(g). The ATPS (at one phase at room temperature) was then added. The ATPS contained either 0.01% FITC-dextrose or FITC-PEG, in order to fluorescently label the specific polymer phase inside the vesicle. In order to see the partitioning of biomolecules that are encapsulated in the liposomes, fluorescently-labeled proteins or DNA were added to the lipid films instead of the fluorescently-labeled polymers. Samples were incubated at room temperature for approximately forty hours in the absence of light.

After encapsulation and swelling has occurred, liposomes were cooled in the refrigerator (3° C.) until two phases in the bulk solution formed. The pink liposomal "cloud" was removed and was either diluted with cold 0.5M sucrose. The liposomes were then viewed using the optical microscope.

EXAMPLE 3

Encapsulation of Biomolecules

It is expected that fluorescently-labeled polymers would partition into their respective phases. In order to see the effects of chemical reactions within a crowded, confined environment, the partitioning of biomolecules involved was first investigated. The two DNA strands had the best partitioning of the biomolecules studied. All experiments were performed in the absence of salt. In photographs taken under an optical microscope of the encapsulated 88-base oligonucleotide, the partitioning is easily visible and the two phases can be distinguished. As expected the DNA partitions into the outer dextran-rich phase. The 12-base oligonucleotide follows the same trend. These images show the creation of microcompartmentation of biomolecules within synthetic cells, mimicking the conditions created by the cytoplasm in living cells.

The intensity of fluorescence versus position was graphed. This quantitative data was used to calculate an approximate partition coefficient by averaging the intensities of the 6-FAM DNA in both the inner and outer phases. Confocal microscopy gives a more accurate quantitative intensity because it rejects out-of-focus light due to the use of a laser to focus on set focal planes in the sample. A ratio was calculated for multiple liposomes and averaged together. The average partition coefficient was calculated to be K=0.5+/−0.1. This is compared to 0.86+/−0.01, the partition coefficient of the 88-base DNA partitioned in bulk ATPS. The improvement in partitioning for the encapsulated ATPS shows the effect of the sucrose addition.

In bulk partitioning experiments, the partition coefficients of the proteins studied did not deviate greatly from 1. However, the addition of sucrose should have helped improve the partitioning. The DIC image shows that the ATPS has separated into two phases. In the fluorescence image, partitioning is not as visible as with the DNA encapsulated liposomes. There is a slightly higher intensity of FITC-BSA in the outer phase. For the catalase and HRP encapsulation, no partitioning was visible. There was phase separation of the ATPS (seen in DIC image), but the biomolecules partitioned evenly between the two phases. This is expected and follows the trend observed in bulk ATPS.

A variety of methods are available to improve biomolecule partitioning in aqueous phase systems. These include the addition of solutes such as salts or other small molecules, chemical modification of one or more of the polymers to increase attractive or repulsive interactions with biomolecules, and chemical modification of the biomolecules of interest to target one of the phases or the interface. These methods have been described in detail in the literature; an introduction can be found in Zaslavsky *Aqueous Two Phase Partitioning: Physical Chemistry and Bioanalytical Applications*, Marcel Dekker: New York, 1995 and Methods in Enzymology volume 228, *Aqueous Two Phase Systems*, Edited by H. Walter and G. Johansson, Academic Press:New York, 1994, the disclosures of which are hereby expressly incorporated by reference.

In addition to these methods, a new method has been developed for dramatically improving biomolecule partitioning within aqueous two phase systems with compositions near the binodal. Biomolecules are conjugated to colloidal gold nanoparticles prior to putting them in the ATPS. Biomolecule: Au nanoparticle conjugates partition very strongly, such that the deep red color of the gold nanoparticles is easily visible (by the naked eye or spectrometer) in only one of the phases, and the other phase remains clear. This approach has been used by the inventors to partition DNA oligonucleotide-coated nanoparticles into the dextran-rich phase, and horseradish peroxidase-coated gold nanoparticles into the PEG-rich phase of bulk PEG/dextran ATPS. Biomolecule: nanoparticle conjugates are well known in the literature and methods for their preparation have been described in detail.

For an introduction, see: *Colloidal Gold: Principles, Methods and Applications*; Hayat, M. A., Ed. Academic Press:San Diego, 1989; vols 1-3.

EXAMPLE 4

Reversible Phase Formation in ATPS/GUV by Varying External Osmotic Pressure

The internal, phase separated ATPS within GUVs can be converted to a single phase by placing the ATPS/GUV into a hypotonic solution, which has a lower osmotic pressure than the internal solution. The lipid bilayer acts as a semipermeable membrane, allowing water to pass quickly but retarding or preventing the movement of solutes (such as polymers) across the membrane. Thus, water flows into the GUV, diluting the internal solution. For an ATPS composition near the bimodal curve on the phase diagram, a small dilution will cause the ATPS to convert to a single phase. This approach has been successfully used to convert ATPS/GUVs to single-phase systems. In the example system, a small amount of deionized water was added to the external solution, however any hypotonic solution can be used for the same result. The degree to which the osmotic pressure inside and outside the vesicle differ will determine the degree to which the internal contents of the GUVs are diluted.

It is also possible to reverse this process, and induce phase separation in an initially single phase GUV if the encapsulated polymer solution is not too far from the bimodal curve in composition. To accomplish this, a hypertonic sucrose solutions is added to the external solution of the vesicles. Under the optical microscope, it is apparent that the vesicles shrink in response to the hypertonic external solution. As water is removed from the vesicle interiors, the polymers become concentrated and at some point phase separation occurs. Any hypertonic solution could be used to accomplish this conversion, with the osmotic pressure more critical than the nature of the molecules used as solutes (osmotic pressure is a olligative property).

To accurately determine the osmotic pressure of the internal polymer solution (in order to prepare external solutions of appropriate osmotic pressure to achieve desired conversions from one to two phases or the reverse), vapor phase osmometry may be used. This method is accurate for nonideal solutions such as the polymer solutions used to prepare ATPS. It is important not to make the disparity in osmotic pressure on the inside and outside of the membrane too great, or vesicle rupture may be observed (e.g. due to the vesicle swelling beyond the lipids ability to contain the volume).

More elaborate schemes can be envisioned in which pores in the vesicle membrane selectively pass ions or solvent molecules to impact the phase behavior of the interior polymeric solution.

This approach could be used to reversibly partition biomolecules or particles into separate phases and then allow them to mix in a single phase based on the osmotic pressure of the external solution. It is possible to control biomacromolecule association and therefore activity by controlling partitioning within these synthetic cells.

EXAMPLE 5

Conversion of Biphasic ATPSs to Monophasic Systems

Conversion of biphasic ATPS to monophasic system within GUV ATPS for which the bimodal curve is responsive to temperature can be converted between one and two phases after encapsulation within a GUV (or other microvolume). This is done simply by changing the temperature from one where the ATPS exists as a single phase to one where it exists as two (or more) phases, or vice versa. This approach has been used to convert PEG/dextan ATPS-containing GUVs to single-phase containing GUVs by elevating the temperature to 16° C. or ~37° C., depending on the encapsulated ATPS composition. It should be noted that it cannot be assumed that all vesicles within a given preparation will contain ATPS of identical composition, despite having been prepared at the same time from a single aqueous phase that phase separated upon cooling (or heating). This must be considered when chosing temperatures for conversion of ATPS/GUV between one and two (or more) phases.

EXAMPLE 6

Altering Macromolecule Partitioning within Encapsulated ATPS

Protein translocation within living cells can lead to sigmoidal ("switchlike") response curves, as opposed to the typical Michaelis-Menton kinetics. Indeed, the localization and movement of signaling proteins within the cell is an area of intense research. It is possible to model this important aspect of cell behavior in the synthetic systems of this invention by altering protein partitioning in the encapsulated ATPS.

Temperature, salt concentration, polymer concentration, and other solution variables can alter partitioning of macromolecular solutes such as proteins in ATPS. The object is to etermine which of these variables are most amenable to use in liposome-encapsulated ATPS. Theief constraints are the preparation procedure, which limits the ATPS compositions that can be used, and the lipid membrane itself, which limits the ability to rapidly and reversibly modify the internal solution composition. In addition, the ability of the lipid membrane to deform, for example allowing the PEG-rich phase to be expelled from the main ATPS-containing compartment into an attached, separate compartment, is an additional challenge. Reversibly altering partitioning does not require conversion from a biphasic to a monophasic system, although this is one way of achieving it.

The phase behavior of encapsulated polymer solutions will be controlled by dilution or ion composition of the solution. For example, the external solution could be diluted, such that $H_2O$ enters the vesicles by osmosis to dilute the ATPS below its critical point, converting it to a single phase. Addition of salt or other solutes (e.g. sucrose) to the external solution would reverse the process, returning the encapsulated solution to two phases.

A more selective means of controlling the phase behavior of internal polymer solution is the incorporation of protein or peptide ion channels within the lipid bilayer. Several pore-forming peptides/proteins are commercially available, and many more can be purified from bacterial sources. For example, the commercially available and water-soluble α-hemolysin (α-HL), forms monoheptameric 1 to 2 nm inner diameter pores that permit transport of molecules as large as 3000 g/mol. α-HL will be incorporated in liposomal membranes by addition of the protein to preformed vesicles in polymer/buffer solution. Note that the Bailey group has generated a variety of molecule-selective variants of α-HL, and has demonstrated their use in sensing.(Bayley, H.; Cremer, P. S. "Stochastic sensors inspired by biology" *Nature* 2001, 413, 226-230.; Walker, B.; Kasianowicz, J.; Krishnasastry, M.; Bayley, H. "A pore-forming protein with a metal-actuated switch" *Protein Eng.* 1994, 7, 655-662.; Chang, C.; Niblack, B.; Walker, B.; Bayley, H. "A photogenerated pore-forming protein" *Chem. Biol.* 1995, 2, 391-400.; Walker, B.; Bayley, H. "A pore-forming protein with a protease-activated trigger" *Protein Eng.* 1994, 7, 91-97.)

In order to respond to stimuli, cells must first detect that a change in environment has occurred. This function will be incorporated into cytomimetic assemblies by controlling macromolecule location/aggregation. Enzyme translocation is one way of turning a normal, Michaelis-Menton type response into one that displays ultrasensitivity. The physical proximity of many enzymes that function in metabolic pathways can give rise to "substrate channeling", in which the product of one enzymatic reaction is "handed off" as the substrate to another enzyme without freely diffusing throughout the cell. Spivey, H. O.; Ovadi, J. "Substrate channeling" *Methods* 1999, 19, 306-321.; Al-Habori, M. "Microcompartmentalization, metabolic channeling, and carbohydrate metabolism" *Int. J. Biochem. Cell Biol.* 1995, 27, 123-132.) This effect has been experimentally modeled by Niemeyer et al., and is one control mechanism for enzymatic pathways in biological systems. Coupled enzymatic reactions yield more rapid product formation when co-localized. More importantly, control over association can act as a sensitive switch to turn on/off a reaction pathway, and should become striking as the number of enzymes in the reaction chain is increased above three or four. For lower numbers of enzymes, the rate enhancement should be measurable but not dramatic.

These effects will be taken advantage of to construct cytomimetic sensors based on altering the association of enzyme partners. A two enzyme system, glucose oxidase (GOx) and horseradish peroxidase (HRP) will be the starting point. $GO_x$ converts glucose and $O_2$ to gluconic acid lactone and $H_2O_2$. HRP can be used to convert $H_2O_2$ and an organic substrate into a fluorescent product. 4-acetamidophenol will be used as an HRP substrate; upon reaction a dimer is produced which, when illuminated at 328 nm fluoresces at 431 nm. Other substrates can also be used; an advantage of the 4-acetamidophenol is that the product gives maximum fluorescence intensity near neutral pH. Although these two enzymes are not coupled in biological systems, it should be possible to control their association using either phase separation or volume exclusion, and thereby to control the production of fluorescent product. GOx and HRP are very well characterized and commercially available with a variety of covalent modifications.

GOx and HRP will be incorporated into GUVs during vesicle swelling at 25° C. (or 4° C., once an appropriate ATPS is identified). The success of incorporation will be monitored by fluorescence microscopy, using fluorophore-tagged HRP and GOx. Although it is difficult to accurately measure the enzyme concentration within a single GUV, due to the large size of these vesicles the internal composition can be reasonably assumed to match that of the aqueous phase during preparation. Enzyme-containing GUVs will be separated from unincorporated enzymes by collection of the GUV-rich "white cloud" from the interface after vesicle preparation, and dilution into enzyme-free solution. After mounting the GUV sample under the microscope, the reaction will be followed by fluorescence after initiation by adding glucose to the external medium. Jones and Kaszuba have monitored $H_2O_2$ production from ~100 nm HRP/GOx-containing liposomes via electrochemistry. Their liposome preparation protocol will be modified, which uses saturated lipids to prevent oxidation damage to the bilayer. Two separate sensor designs are envisioned.

Approach 1. Phase behavior-based switching is one possible mechanism for metabolite channeling in vitro, and perhaps in vivo. Enzymes will be targeted to the different phases and their activities monitored as a function of the presence/absence of a phase boundary. Transitioning between one and two phases, as described in the previous section, will lead to mixing or demixing of the enzymes. Two strategies are illustrated in Scheme II. In the first, both enzymes are partitioned into a single, very low volume phase. This will be achieved by using affinity tags and ionic strength to modulate partitioning, and tie line information to control phase volumes. Upon dilution the ATPS will become one phase, greatly magnifying the dilution effect felt by the enzymes, and dramatically reducing product formation. In the second strategy, the two enzymes are targeted to different phases, and mix upon the disappearance of the phase boundary to turn on-production of the fluorescent product. We will measure the rate of 4-acetamidophenol dimerization in bulk for both single- and two-phase systems to determine the magnitudes of difference upon phase separation/mixing. The effect may be different in microvolumes, as interaction with the membrane wall is possible, and the interfacial surface area is much larger with respect to ATPS volume.

Approach 2: Volume exclusion-based switching. Two phases are not required for construction of translocation-based sensors. Volume exclusion alone can drive macromolecule association at concentrations too low for aggregation in the absence of volume excluders; under these conditions small changes in dilution can be used to control the extent of protein association. We will design a sensor based on this principle. The rate of final product formation is expected to increase with enzyme proximity, as the intermediate compounds no longer must diffuse over large distances to reach the next enzyme in the chain. Two possibilities can be envisioned: (i) an increase in volume exclusion turns on the fast production of product by causing the association of the multiple enzymes, and (ii) a decrease in volume exclusion turns off/slows the reaction by causing the dissociation of the enzymes. Reactions will first be carried out in bulk solution to determine what amount of volume excluding polymer (e.g. PEG) would be necessary to cause enzyme association, and what increase in reaction rate can be expected as a result.

For either approach described here, the most straightforward means of altering the macromolecular interactions is by dilution/concentration. Thus, we will have synthesized internal volume sensors. Cell volume in living organisms is tightly regulated, and mechanisms such as those described above may play a role in this regulation and/or serve as an explanation for the precision with which cell volume is regulated. By coupling this volume sensor with membrane channels, sensitivity to other stimuli could be incorporated. Incorporating more elaborate multienzyme chains would lead to improved sensitivity due to greater number of interacting enzymes in the "pathway".

Living cells respond to detected stimuli by, e.g., movement, production of chemicals, etc. In the synthetic "cells", the association of biomacromolecules could ultimately be set up to produce, e.g., a drug rather than a fluorescent molecule. The reversible stimulus-dependent association of biomacromolecules has many implications beyond simple cytomimetic sensing; indeed, it has the potential to power liposomal motion.

EXAMPLE 7

Reversible Polymerization of Cytoskeletal Proteins Within Synthetic "Cells"

Cell locomotion is one of the most intriguing of cell functions. The initial steps toward mimicking cell crawling will be taken in the synthetic systems. Volume exclusion will be used to control polymerization of vesicle-encapsulated tubulin much as described for enzymes in the previous section. No ATPS is necessary for the proposed experiments, although the behavior of polymerizing cytoskeletal fibers in ATPS will also be investigated and may prove interesting.

Volume exclusion has been shown to impact the association of this and other cytoskeletal proteins. The cytoskeletal protein, tubulin, is important for flagella-driven movement and for the transport of vesicles within the cytoplasm. Tubulin can be reversibly polymerized in vitro by changing the solution temperature (the protein polymerizes when warm and depolymerizes when cold; indeed, this phenomenon is employed in its purification). Several groups have encapsulated tubulin within GUVs and observed deformations of the lipid bilayer upon polymerization. Tubulin will be encapsulated within GUVs and control its polymerization by varying the degree of macromolecular crowding within the liposome as described in the previous section. The resulting morphologies will be compared with the effect of temperature on encapsulated tubulin.

Directional "Cell Crawling" It is possible to control the motion of the "cells" on a planar substrate. The substrate would be coated with a gradient of weak binding sites for functional groups incorporated in the bilayer membrane of the synthetic cell. The "cell" would be adherent on the substrate, and bind to several of these functional groups. Upon stimulation, tubulin would begin polymerizing, deforming the "cell", such that the membrane has greater contact with the surface after polymerization. Upon a change in the external environment, the microtubules would begin depolymerizing, such that the "cell" regains its spherical initial shape. However, the membrane in contact with the surface will have bound to several of the weak attachment sites and will resist losing contact with the surface, to an extent dependent upon the number of attachment sites. If this experiment is conducted on a substrate coated with a gradient of weak binding sites, the "cell" will ultimately crawl towards the higher density of binding sites.

If the increase in contact area was not sufficient to drive locomotion as described above, the buffer concentration outside the vesicles could be increased slightly to draw water from the vesicles, creating "excess membrane area", such that deformation of the lipid bilayer will require less energy. Indeed, larger periodic changes in buffer osmolarity are expected to result in liposomal motion along the gradient even in the absence of internal cytoskeletal polymerization, as this would cause the contact area with the surface to increase and decrease alternately. Motion directed by reversible polymerization of vesicle contents, however, has the potential for ultrasensitive (sigmoidal) response curves that could ultimately linked to more interesting stimuli, as noted in the previous section.

Cell crawling in vivo requires the reversible polymerization of another cytoskeletal protein, actin. Actin can also be incorporated within liposomes. We have chosen tubulin for the initial experiments because actin filaments typically do not deform the vesicle to the same extent as microtubules. Nonetheless they do result in altered morphology, and could be used in a similar fashion.

EXAMPLE 8

DNA-Directed Nanoparticle Assembly at the Interface of an ATPS

Au nanowires, 2-3 μm in length, were prepared by a templated synthesis method using aluminum oxide membranes (for ~300 nm diameter wires) or polycarbonate membranes (~70 nm diameter wires). Once extracted from the host membrane, the nanowires were derivatized with NeutrAvidin™ biotin-binding protein followed by 5' biotinylated DNA (5' biotinyl AAA AAA CGC ATT CAG GAT 3')(SEQ ID NO:3). DNA-coated Au nanowires at the aqueous/aqueous interface formed in an ATPS comprising 15 wt % of each 8 kDa polyethylene glycol and 144 kDa dextran in hybridization buffer (0.3 M NaCl/10 mM phosphate buffer, pH 7). In this case, nanowire packing was driven not by specific DNA interactions (the DNA on the wires was not self-complementary), but rather by the high concentration of wires at the interface.

To verify that nanoparticle-bound oligonucleotides located at the interface retain their ability to selectively hybridize to complementary DNA strands, a fluorescently labeled oligonucleotide was added to an ATPS where DNA-coated Au oligonucleotide was added to an ATPS where DNA-coated Au wires had previously settled at the interface. After hybridizing overnight, the Au wires were extracted from the interface and rinsed to remove polymer and unbound fluorescent DNA. Fluorescence microscopy indicated that hybridization of the labeled complement to the nanowires at the interface was successful.

Experimental Methods

Nanowire Synthesis

The larger diameter Au nanowires used in the experiments reported here were grown galvanostatically in commercial aluminum oxide membranes (Whatman) with pore diameters nominally 300 nm. The wires were grown for 40-60 minutes, which resulted in lengths between 2-3 microns. Commercially available polycarbonate membranes were used to grow the 70 nm diameter wires using a three electrode potentiostatic deposition, where an evaporated silver film on the backside of the polycarbonate membrane was used as the working electrode, a Pt mesh was used as the counter and an Ag/AgCl electrode was used as the reference. Au (Orotemp 24) and Ag (1025 RTU) plating solutions were purchased from Technic Inc. The resulting particles were then extracted from the host template by dissolution in NaOH for the alumina membranes or dissolution in methylene chloride for the polycarbonate templates, and dispersed in water.

Nanowire Derivatization

NeutrAvidin™ was directly adsorbed onto the nanowire surface by tumbling the wires in a 0.5 mg/ml NeutrAvidin™ (Pierce) solution for two hours before the excess protein was removed by centrifugation. The protein covered wires were tumbled with 10 nM of biotinylated oligonucleotide overnight. For the hybridization and assembly experiments, the oligo sequence (purchased from IDT Technologies, Inc.) used was 5' Biotin AAA AAA CGC ATT CAG GAT, (SEQ ID NO:3), where the six A bases at the 5' end act only as a spacer in these experiments. Excess DNA was removed by centrifugation and removal of supernatant three times.

ATPS Formation

Aqueous two phase systems were prepared by mixing equal portions of 15% w/w % dextran (144K) and 15% w/w % PEG(8000). The polymers were purchased from Aldrich and were prepared by dissolving in hybridization buffer (pH 7, containing 10 mM phosphate buffer and 0.3 M NaCl). These polymer solutions are prone to bacterial contamination, therefore solutions were made fresh before each experiment, or were stored at 4° C. Equal weights of the two polymers were placed into a glass vial or Eppendorf tube, mixed together and left to separate completely before the addition of the DNA coated nanoparticles.

Fluorescent Hybridization Experiments

Wires were first pipetted on top of the aqueous two-phase systems and left to settle to the interface. For the fluorescence hybridization experiments, fluorescently labeled DNA was added to the top phase of the ATPS and left to hybridize with the wires at the interface for up to 36 hours. Wires extracted from the interface were spun down and the excess unbound DNA was removed with the supernatant. The wires were washed three times in fresh buffer before a small aliquot was placed on a glass cover slip and imaged using a 100× oil immersion lens on an inverted fluorescent microscope, using a xenon illumination source. Sequences used for hybridization were: 5' TAMRA ATC CTG AAT GCG (SEQ ID NO:4) and a 5' TAMRA GCA ACG GCC TAG (SEQ ID NO:5) control strand, where TAMRA denotes tetramethyl rhodamine.

Wire Colloid Assembly Experiments

DNA coated Au nanowires were added to an ATPS system and left to settle to the interface before Au:DNA conjugates and a linker sequence were added. The DNA:Au conjugates used were prepared using a modified Mirkin procedure as described in references 6 and 7, and consisted of 12 nm Au colloid surrounded by thiolated DNA with sequence 3' Thiol TCT CAA CTC GTA (SEQ ID NO:6). The wires and colloid were left to assemble at the interface for at least 24 hours. Thermal denaturation experiments were performed on an HP 8453A diode array spectrometer, equipped with a Peltier cell. The rod-colloid aggregate was extracted from the interface, spun down and resuspended in hybridization buffer three times and then placed in a quartz cuvette. The temperature was ramped up at 1° C./min with a hold time of 2 minutes from 40-70° C., and the absorbance at 520 nm was measured at each temperature, and referenced at 900 nm.

It should be appreciated that minor modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A microscopic volume comprising:
a synthetic vesicle encapsulating an aqueous system, said aqueous system comprising two or more chemically dissimilar polymers, and further providing that said aqueous system forms at least a two-phase interface between the polymers depending upon one or more of the factors selected from the group consisting of temperature and composition of the microscopic volume, said polymers capable of converting to a single phase in the vesicle above the phase transition temperature then returning to a multiphase system in the vesicle upon cooling to a temperature below the phase transition temperature; said interface having an interfacial tension of between about 0.0001-0.1 dyne/cm.

2. The microscopic volume of claim 1 whereby the chemically dissimilar polymers are a polymer/polymer combination, or a polymer/salt combination.

3. The microscopic volume of claim 2 whereby the polymer/polymer combination is comprised of a polyethylene glycol and a dextran.

4. The microscopic volume of claim 1 whereby the aqueous system is biocompatible.

5. The microscopic volume of claim 1 whereby the aqueous system is capable of converting to a single phase at a first temperature, then returning to multiple phases at a second temperature.

6. The microscopic volume of claim 1 whereby at least one biological macromolecule is partitioned within the vesicle.

7. The microscopic volume of claim 6 wherein the biological macromolecule is one or more selected from the group consisting of DNA, RNA, protein, and an enzyme.

8. The microscopic volume of claim 6 that includes more than one biological macromolecule, whereby the macromolecules are partitioned within the same phase or different phases.

9. The microscopic volume of claim 7 whereby the proximity of different biological macromolecules is controlled by phase separation.

10. The microscopic volume of claim 1 whereby the vesicle is comprised of a single lipid bilayer.

11. The microscopic volume of claim 10 whereby the lipid bilayer is comprised of a 1,2-oleoyl-sn-glycero-3-phosphocholine/1,2-dioleoyl-sn-glycero-3-[phospho-RAC-(1-glycerol)] mixture.

12. The microscopic volume of claim 1 whereby the vesicle includes one or more functionalized groups selected from the group consisting of cholesterol, polymer-modified headgroups, fluorophore-modified headgroups or tails, and carbohydrate functionalized groups.

13. The microscopic volume of claim 10 whereby the lipid bilayer is unilamellar or multilamellar.

14. The microscopic volume of claim 10 whereby the lipid bilayer further contains one or more from the group consisting of proteins and peptides.

15. The microscopic volume of claim 14 whereby the proteins and/or peptides form pores in the lipid bilayer.

16. The microscopic volume of claim 10 whereby the lipid in the lipid bilayer is polymerized.

17. The microscopic volume of claim 1 whereby the vesicle is comprised of copolymers.

18. A microscopic volume according to claim 1 whereby the chemically dissimilar polymers are selected from the group consisting of cashew-nut tree gum/PEG, PEG/polyacrylamide, starch/PEG, cellulose/dextran, polysaccharides/

PEG, agar/starch, dextran/polyethylene glycol polypropylene glycol copolymer, dextran/polyvinylalcohol, dextran/benzoyldextran, dextan/ficoll, hydroxypropyl starch/PEG, polyvinylalcohol/PEG, maltodextran/PEG, pullulan/PEG, poly(vinyl methyl ether)/PEG, dextran sulfate/PEG, carboxymethyldextran/PEG, dextran sulfate/polystyrene sulfonate, potassium phosphate/PEG, ammonium sulfate/PEG, potassium citrate/PEG, and magnesium sulfate/PEG.

19. A freestanding two-dimensional assembly comprising: a synthetic, aqueous, multi-phase system comprising two or more chemically dissimilar polymers, said system having a two-phase interface between the polymers; and particles on said interface, said polymers capable of converting to a single phase in the vesicle above the phase transition temperature then returning to a multiphase system in the vesicle upon cooling to a temperature below the phase transition temperature; said interface having an interfacial tension of between about 0.0001-0.1 dyne/cm; whereby the chemically dissimilar polymers are selected from the group consisting of cashew-nut tree gum/PEG, PEG/polyacrylamide, starch/PEG, cellulose/dextran, polysaccharides/PEG, agar/starch, dextran/polyethylene glycol polypropylene glycol copolymer, dextran/polyvinylalcohol, dextran/benzoyldextran, dextan/ficoll, hydroxypropyl starch/PEG, polyvinylalcohol/PEG, maltodextran/PEG, pullulan/PEG, poly(vinyl methyl ether)/PEG, dextran sulfate/PEG, carboxymethyldextran/PEG, dextran sulfate/polystyrene sulfonate, potassium phosphate/PEG, ammonium sulfate/PEG, potassium citrate/PEG, and magnesium sulfate/PEG.

20. A microscopic volume comprising: a synthetic vesicle encapsulating an aqueous system, said aqueous system comprising two or more chemically dissimilar polymers, and further providing that said aqueous system forms at least a two-phase interface between the polymers depending upon one or more of the factors selected from the group consisting of temperature and composition of the microscopic volume, said polymers capable of converting to a single phase in the vesicle above the phase transition temperature then returning to a multiphase system in the vesicle upon cooling to a temperature below the phase transition temperature; said vesicle having at least one protein biomolecule partitioned within, and further providing that hydrogen bonding occurs between the polymers and water molecules present in the aqueous system.

21. A freestanding two-dimensional assembly comprising: a synthetic, aqueous, multi-phase system comprising two or more chemically dissimilar polymers, said system having a two-phase interface between the polymers, said polymers capable of converting to a single phase in the vesicle above the phase transition temperature then returning to a multiphase system in the vesicle upon cooling to a temperature below the phase transition temperature; and particles on said interface; said interface having an interfacial tension of between about 0.0001-0.1 dyne/cm.

22. An assembly according to claim 21 whereby the chemically dissimilar polymers are selected from the group consisting of cashew-nut tree gum/PEG, PEG/polyacrylamide, starch/PEG, cellulose/dextran, polysaccharides/PEG, agar/starch, dextran/polyethylene glycol polypropylene glycol copolymer, dextran/polyvinylalcohol, dextran/benzoyldextran, dextan/ficoll, hydroxypropyl starch/PEG, polyvinylalcohol/PEG, maltodextran/PEG, pullulan/PEG, poly(vinyl methyl ether)/PEG, dextran sulfate/PEG, carboxymethyldextran/PEG, dextran sulfate/polystyrene sulfonate, potassium phosphate/PEG, ammonium sulfate/PEG, potassium citrate/PEG, and magnesium sulfate/PEG.

23. The assembly of claim 21 whereby the chemically dissimilar compounds are polymers or a polymer/salt combination.

24. The assembly of claim 23 whereby the polymer combination is comprised of a polyethylene glycol and a dextran.

25. The assembly of claim 21 whereby the aqueous multi-phase system is biocompatible.

26. The assembly of claim 21 whereby the particles are from about 1-400 nm in diameter.

27. The assembly of claim 21 whereby the particles are selected from the group consisting of metal, semiconductor, and magnetic.

28. The assembly of claim 21 whereby a compound selected from one or more of the group consisting oligonucleotides, antibodies, enzymes, and proteins are attached to the particles.

29. The assembly of claim 21 whereby the particles are bound by biorecognition.

30. A method of making microscopic volumes comprising: forming an aqueous multi-phase system using chemically dissimilar compounds; altering one or more factors selected from the group consisting of temperature and composition of the agents to form a single phase system; adding the single phase system to one or more vesicle-forming compounds to form a mixture; allowing the mixture to hydrate for a time period sufficient to form at least one vesicle; and altering one or more factors selected from the group consisting of temperature and composition of the compounds to reform a multi-phase system; whereby the aqueous multi-phase system is encapsulated by the vesicle.

31. The method of claim 30 whereby the chemically dissimilar compounds are chosen by performing titrations of the compounds to form binodals; and selecting agents that fall between the binodals.

32. The method of claim 31 whereby the chemically dissimilar compounds are a polymer combination, or a polymer/salt combination.

33. The method of claim 32 whereby the polymer combination is comprised of a polyethylene glycol and a dextran.

34. The method of claim 30 further comprising: incorporating functional groups into the vesicle by mixing the functional groups with the vesicle-forming compounds prior to the hydration step.

35. The method of claim 16 further comprising mixing fluorescently-tagged polymers into the chemically dissimilar compounds during the formation of the aqueous multi-phase system.

36. A method of making a freestanding two-dimensional assembly comprising: forming an aqueous multi-phase system having an interface using chemically dissimilar compounds; and assembling particles on the interface.

37. The method of claim 36 whereby the chemically dissimilar compounds are a polymer combination, or a polymer/salt combination.

38. The method of claim 37 whereby the polymer combination is comprised of a polyethylene glycol and a dextran.

39. The method of claim 36 whereby the particles are nanoparticles.

40. The method of claim 39 whereby the nanoparticles are selected from the group consisting of metal, semiconductor, magnetic, polymeric, and microscopic volumes.

41. The method of claim 36 whereby oligonucleotides are attached to the particles.

42. The method of claim 36 whereby the particles are bound by biorecognition.

43. The method of claim 36 whereby the particles are bound by chemical derivatization.

44. The method of claim 43 whereby the particles are colloidal gold nanoparticles conjugated to biomolecules.

45. The method of claim 36 whereby the assembled particles are used as a nucleation site for chemical reduction of metal.

46. The method of claim 36 further including the step of: removing the assembled particles from the interface.

47. The method of claim 46 whereby the assembled particles are removed from the interface by a method selected from the group consisting of diluting the aqueous multi-phase system and heating the assembled particles.

* * * * *

UNITED STATES PATENT AND TRADEMARK OFFICE
CERTIFICATE OF CORRECTION

PATENT NO. : 7,803,405 B2  
APPLICATION NO. : 10/439578  
DATED : September 28, 2010  
INVENTOR(S) : C. D. Keating et al.

Page 1 of 1

It is certified that error appears in the above-identified patent and that said Letters Patent is hereby corrected as shown below:

On the Title page, Item (60), Related U.S. Application Data
DELETE: "60/283,431"
ADD: --60/382,431--

In the Claims

Col. 34, Claim 40, Line 61
DELETE: "claim 39"
ADD: --claim 35--

Signed and Sealed this
Sixteenth Day of July, 2013

Teresa Stanek Rea
*Acting Director of the United States Patent and Trademark Office*